United States Patent
Lee et al.

(10) Patent No.: US 10,276,807 B2
(45) Date of Patent: Apr. 30, 2019

(54) LIGHT-EMITTING LAYER FOR PEROVSKITE LIGHT-EMITTING DEVICE, METHOD FOR MANUFACTURING SAME, AND PEROVSKITE LIGHT-EMITTING DEVICE USING SAME

(71) Applicant: POSTECH ACADEMY-INDUSTRY FOUNDATION, Pohang-si, Gyeongsangbuk-do (KR)

(72) Inventors: Tae-Woo Lee, Pohang-si (KR); Sanghyuk Im, Hwaseong-si (KR); Himchan Cho, Daegu (KR); Young-Hoon Kim, Daejeon (KR)

(73) Assignee: POSTECH ACADEMY-INDUSTRY FOUNDATION, Pohang-si, Gyeongsangbuk-Do (KR)

( * ) Notice: Subject to any disclaimer, the term of this patent is extended or adjusted under 35 U.S.C. 154(b) by 0 days.

(21) Appl. No.: 15/524,489

(22) PCT Filed: Nov. 6, 2015

(86) PCT No.: PCT/KR2015/011963
§ 371 (c)(1),
(2) Date: Jul. 26, 2017

(87) PCT Pub. No.: WO2016/072809
PCT Pub. Date: May 12, 2016

(65) Prior Publication Data
US 2017/0358759 A1    Dec. 14, 2017

(30) Foreign Application Priority Data

Nov. 6, 2014   (KR) .................. 10-2014-0153965
Nov. 6, 2015   (KR) .................. 10-2015-0156173

(51) Int. Cl.
*H01L 31/00*    (2006.01)
*H01L 51/00*    (2006.01)
(Continued)

(52) U.S. Cl.
CPC .......... *H01L 51/0077* (2013.01); *C01G 21/16* (2013.01); *C07F 7/24* (2013.01);
(Continued)

(58) Field of Classification Search
CPC ............ H01L 51/0077; H01L 51/0037; H01L 51/004; H01L 51/0059; H01L 51/0034;
(Continued)

(56) References Cited

U.S. PATENT DOCUMENTS 6,777,871 B2 *   8/2004   Duggal ................. B82Y 20/00
                                               313/504
9,109,153 B2 *   8/2015   Shin ....................... B82Y 30/00
(Continued)

FOREIGN PATENT DOCUMENTS

JP    2009-006548       1/2009
KR    10-2001-0015084   2/2001
KR    10-2010-0034003   3/2010

OTHER PUBLICATIONS

Schmidt et al., "Nontemplate Synthesis of CH3NH3PbBr3 Perovskite Nanoparticles", 2014, J. Am. Chem. Soc., 2014, 136 (3) pp. 850-853, Publication Date : Jan. 3, 2014.*
(Continued)

*Primary Examiner* — Nikolay K Yushin
(74) *Attorney, Agent, or Firm* — Knobbe Martens Olson & Bear LLP

(57) ABSTRACT

Disclosed are a light-emitting layer for a perovskite light-emitting device, a method for manufacturing the same, and a perovskite light-emitting device using the same. The method of manufacturing the light-emitting layer comprises
(Continued)

a step of forming a first nanoparticle thin film by coating, on a substrate for coating a light-emitting layer, a solution comprising organic and inorganic perovskite nanoparticles. Thereby, a nanoparticle light emitter has therein an organic and inorganic hybrid perovskite having a crystalline structure in which FCC and BCC are combined, and has a lamella structure in which an organic plane and an inorganic plane are alternatively stacked. Also, high color purity is realized because excitons are confined to the inorganic plane.

26 Claims, 15 Drawing Sheets

(51) Int. Cl.
| | | |
|---|---|---|
| C07F 7/24 | (2006.01) | |
| C09K 11/66 | (2006.01) | |
| B82Y 40/00 | (2011.01) | |
| C01G 21/16 | (2006.01) | |
| C09K 11/06 | (2006.01) | |
| H01L 51/50 | (2006.01) | |
| C09K 11/02 | (2006.01) | |
| B82Y 20/00 | (2011.01) | |
| B82Y 30/00 | (2011.01) | |
| H01L 51/42 | (2006.01) | |
| H01L 51/44 | (2006.01) | |
| H01L 51/52 | (2006.01) | |

(52) U.S. Cl.
CPC ............ *C09K 11/025* (2013.01); *C09K 11/06* (2013.01); *C09K 11/665* (2013.01); *H01L 31/00* (2013.01); *H01L 51/004* (2013.01); *H01L 51/0034* (2013.01); *H01L 51/0037* (2013.01); *H01L 51/0072* (2013.01); *H01L 51/502* (2013.01); *B82Y 20/00* (2013.01); *B82Y 30/00* (2013.01); *B82Y 40/00* (2013.01); *C01P 2002/34* (2013.01); *C01P 2002/60* (2013.01); *C01P 2004/64* (2013.01); *C01P 2006/40* (2013.01); *C09K 2211/10* (2013.01); *C09K 2211/188* (2013.01); *H01L 51/0003* (2013.01); *H01L 51/0059* (2013.01); *H01L 51/426* (2013.01); *H01L 51/4273* (2013.01); *H01L 51/442* (2013.01); *H01L 51/5096* (2013.01); *H01L 51/5206* (2013.01); *H01L 2251/308* (2013.01); *Y10S 977/774* (2013.01); *Y10S 977/788* (2013.01); *Y10S 977/813* (2013.01); *Y10S 977/892* (2013.01); *Y10S 977/896* (2013.01); *Y10S 977/948* (2013.01); *Y10S 977/95* (2013.01)

(58) Field of Classification Search
CPC ............ H01L 51/0072; H01L 51/0003; H01L 51/502; H01L 51/5206; H01L 51/5096; H01L 51/426; H01L 51/442; H01L 51/4273; H01L 2251/308; H01L 31/00; H01L 31/055; H01L 31/0547; H01L 31/0263; C09K 11/06; C09K 11/665; C09K 2211/10; C09K 2211/188; C09K 11/025; C07F 7/24; C01G 21/16; C01P 2006/40; C01P 2002/34; C01P 2002/60; C01P 2004/64; B82Y 40/00; B82Y 20/00; B82Y 30/00; Y10S 977/774; Y10S 977/788; Y10S 977/813; Y10S 977/896; Y10S 977/892; Y10S 977/948; Y10S 977/95

See application file for complete search history.

(56) References Cited

U.S. PATENT DOCUMENTS

2001/0033135 A1* 10/2001 Duggal ................. B82Y 20/00
313/506
2010/0129529 A1* 5/2010 Shin ...................... B82Y 30/00
427/66

OTHER PUBLICATIONS

Schmidt, L. C. et al., "Nontemplate Synthesis of CH3NH3PbBr3 Perovskite Nanoparticles", Journal of the American Chemical Society, 2014, vol. 136, No. 3, pp. 850-853 (Publication Date: Jan. 3, 2014).

Stoumpos, C. C. et al., "Crystal Growth of the Perovskite Semiconductor CsPbBr3: A New Material for High-Energy Radiation Detection", Crystal Growth & Design, 2013, vol. 13, No. 7, pp. 2722-2727.

WIPO, International Search Report of PCT/KR2015/011963 dated Mar. 10, 2016.

* cited by examiner

FIG. 15
(a)
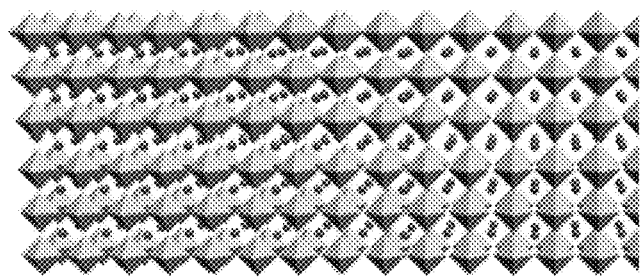
(b)
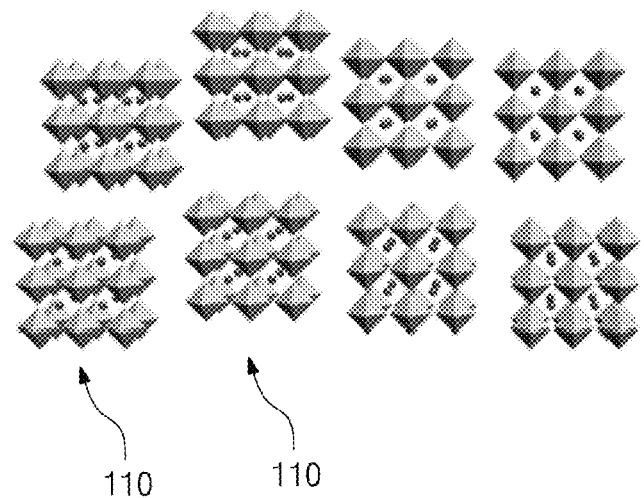
110   110

LIGHT-EMITTING LAYER FOR PEROVSKITE LIGHT-EMITTING DEVICE, METHOD FOR MANUFACTURING SAME, AND PEROVSKITE LIGHT-EMITTING DEVICE USING SAME

TECHNICAL FIELD

The present invention relates to light-emitters and their light emitting device, and more particularly, to a light emitting layer for an organic-inorganic-hybrid perovskite or inorganic metal halide perovskite light emitting device, a method for manufacturing the same, a light emitting device using the same, and a method for manufacturing the light emitting device.

BACKGROUND ART

The major trend of the display market is shifting from the existing high-efficiency and high-resolution-oriented display, to the emotional image-quality display aiming at realizing a high color purity for demonstration of natural colors. From this viewpoint, organic light-emitter-based organic light emitting diode (OLED) devices using organic light-emitters have remarkably developed, inorganic quantum dot LEDs with the improved color purity have been actively researched and developed as alternatives. However, in the viewpoint of emitting materials, both the organic light-emitters and the inorganic quantum dot light-emitters have intrinsic limitations.

The existing organic light-emitter have an advantage of high efficiency, but the existing organic light-emitter have a wide spectrum and poor color purity. Although the colloidal inorganic quantum dot light-emitter have been known to high good color purity because the luminescence occurs by quantum size effects, there is a problem that it is difficult to uniformly control the sizes of the quantum dots as the color approaches the blue color, and thereby the size distribution deteriorate the color purity because of size distribution. Also, both light-emitters (organic emitters and colloidal inorganic quantum dot emitters) are disadvantageously expensive. Thus, there is a need for new types of organic-inorganic-hybrid light-emitter that compensate for the disadvantages of the organic light-emitters and inorganic quantum dot emitters and maintains their merits.

Since the organic-inorganic-hybrid emitting materials have advantages of low manufacturing costs and simple manufacturing and device manufacturing processes and also have all advantages of organic emitting materials, which are easy to control optical and electrical properties, and inorganic emitting materials having high charge mobility and mechanical and thermal stability, the organic-inorganic-hybrid emitting materials are attracting attention academically and industrially.

Among them, since the organic-inorganic-hybrid perovskite materials have high color purity (full width at half maximum (FWHM)≈20 nm), simple color control, and low synthesis costs, the organic-inorganic-hybrid perovskite materials are very likely to be developed as the light-emitter. Since the high color purity from these materials can be realized because they have a layered structure in which a 2D plane made of the inorganic material is sandwiched between 2D planes made of the organic material, and a large difference in dielectric constant between the inorganic material and the organic material is large ($\varepsilon_{organic} \approx 2.4$, $\varepsilon_{inorganic} \approx 6.1$) so that the electron-hole pairs (or excitons) are bound to the inorganic 2D layer.

A material having the conventional perovskite structure ($ABX_3$) is inorganic metal oxide.

In general, the inorganic metal oxides are oxides, for example, materials in which metal (alkali metals, alkali earth metals, lanthanides, etc) cations such as Ti, Sr, Ca, Cs, Ba, Y, Gd, La, Fe, and Mn, which have sizes different from each other, are located in A and B sites, oxygen anions are located in an X site, and the metal cations in the B site are bonded to the oxygen anions in the X site in the corner-sharing octahedron form with the 6-fold coordination. Examples of the inorganic metal oxides include $SrFeO_3$, $LaMnO_3$, $CaFeO_3$, and the like.

On the other hand, since the organic-inorganic-hybrid perovskite has the $ABX_3$ in which organic ammonium ($RNH_3$) cations are located in the A site, and halides (Cl, Br, I) are located in the X site to form the organic-inorganic hybrid metal halide perovskite material, the organic-inorganic-hybrid perovskite are completely different from the inorganic metal oxide perovskite material in composition.

In addition, the materials vary in characteristics due to a difference in composition of the materials. The inorganic metal oxide perovskite typically has characteristics of superconductivity, ferroelectricity, colossal magnetoresistance, and the like, and thus has been generally conducted to be applied for sensors, fuel cells, memory devices, and the like. For example, yttrium barium copper oxides have superconducting or insulating properties according to oxygen contents.

On the other hand, since the organic-inorganic-hybrid perovskite (or inorganic metal halide perovskite) has a structure in which the organic plane (or "A site cation" plane in the perovskite crystal structure) and the inorganic plane are alternately stacked and thus has a structure similar to a lamellar structure so that the excitons are bound in the inorganic plane, it may be an ideal light-emitter that generally emits light having very high purity by the intrinsic crystal structure itself rather than the quantum size effect of the material.

If the organic ammonium (i.e. "A site" cation) in organic-inorganic-hybrid perovskites has a chromophore (mostly including a conjugated structure) which has a bandgap less than that of a crystal structure composed of a central metal and a halogen crystal structure ($BX_6$), the luminescence occurs in the organic ammonium. Thus, since light having high color purity is not emitted, a full width at half maximum of the luminescence spectrum becomes wider than 100 nm. Therefore, the organic-inorganic-hybrid perovskite incorporating the emitting organic ammonium are unsuitable for a light emitting layer. Thus, in this case, it is not very suitable for the light-emitter having the high color purity, which is highlighted in this patent. Therefore, in order to produce the light-emitter having the high color purity, it is important that the luminescence occurs in an inorganic lattice composed of the central metal-halogen elements without containing chromophore in organic ammonium site (i.e. "A site"). That is, this patent focuses on the development of the light-emitter having high color purity and high efficiency in the inorganic lattice. For example, although an organic-inorganic-hybrid material containing an emitting dye is formed in the form of a thin film rather than that of a particle and used as a light emitting layer, the emission originated from the emitting-dye itself, not from the intrinsic perovskite crystal structure as disclosed in Korean Patent Publication No. 10-2001-0015084 (Feb. 26, 2001).

However, because the organic-inorganic-hybrid perovskite has small exciton binding energy, there is a fundamental problem that the luminescence occurs at a low temperature, but the excitons do not emit light at room temperature due to thermal ionization and delocalization of a charge carrier and thus are easily separated as free charge carriers and then annihilated. Also, there is a problem in that the excitons are annihilated by the layer having high conductivity in the vicinity of the excitons after the free charge carriers are recombined again to form excitons. Therefore, to improve luminescence efficiency and luminance of the organic-inorganic-hybrid perovskite-based LED, it is necessary to prevent the excitons from being quenched.

DISCLOSURE OF THE INVENTION

Technical Problem

To solve the abovementioned problems, the present invention provides a light emitting layer for an organic-inorganic hybrid electroluminescence device having improved luminescence efficiency and durability (or stability) by synthesizing organic-inorganic-hybrid perovskite or inorganic metal halide perovskite into a nanocrystals made of at least ternary compounds in unit crystal 3 components) (i.e. perovskite structure) instead of forming a polycrystal thin film in order to prevent thermal ionization, delocalization of charge carriers, and quenching of excitons, a manufacturing the same, a light emitting device, and a method for manufacturing the light emitting device.

Technical Solution

An aspect of the present invention provides a method of a light emitting layer. The method of a light emitting layer includes steps of: preparing a light-emitting-layer coating substrate; and applying a colloidal solution including an organic-inorganic-hybrid perovskite nanoparticles that have an organic-inorganic-hybrid perovskite nanocrystal structure on the light-emitting-layer coating substrate to form a first thin film of a nanoparticles.

The step of forming the first thin film of the nanoparticle may use a solution process, and the solution process may include at least one process selected from the group consisting of spin-coating, bar coating, slot-die coating, Gravure-printing, nozzle printing, ink-jet printing, screen printing, electrohydrodynamic jet printing, and electrospray.

The first thin film of the nanoparticle may have a thickness of 1 nm to 1 μm and surface roughness of 0.1 nm to 50 nm.

The step of forming the first thin film of the nanoparticle may include steps of: preparing an anchoring solution and an colloidal organic-inorganic-hybrid perovskite nanoparticle solution including the organic-inorganic-hybrid perovskite nanocrystal structure; applying the anchoring solution on the light-emitting-layer coating substrate to form an anchoring agent layer; and applying the organic-inorganic-hybrid perovskite nanoparticle solution on the anchoring agent layer to form an anchored light emitting layer. Here, after forming the anchored light emitting layer, the method may further include a step of forming a crosslinking agent layer on the anchored light emitting layer, and the step of applying the organic-inorganic-hybrid perovskite nanoparticle solution and the step of forming the crosslinking agent layer on the layer coated with the organic-inorganic-hybrid perovskite nanoparticle solution may be repeatedly performed to adjust a thickness of the light emitting layer.

The step of forming the first thin film of the nanoparticle may include steps of: mixing an organic semiconductor with the solution including the organic-inorganic-hybrid perovskite nanoparticle to manufacture an organic-inorganic-hybrid perovskite-organic semiconductor solution; and applying the organic-inorganic-hybrid perovskite-organic semiconductor solution to form the light emitting layer. Here, in the step of applying the organic-inorganic-hybrid perovskite-organic semiconductor solution to form the light emitting layer, the light emitting layer may be self-organized in a shape in which an organic semiconductor layer and the organic-inorganic-hybrid perovskite nanoparticle are successively stacked on the light-emitting-layer coating substrate.

The step of forming the first thin film of the nanoparticle may include steps of: forming a self-assembly monolayer on the light-emitting-layer coating substrate; applying a solution including the organic-inorganic-hybrid perovskite nanoparticle on the self-assembly monolayer to form an organic-inorganic-hybrid perovskite nanoparticle layer; and coming into contact with the organic-inorganic-hybrid perovskite nanoparticle layer by using a stamp to remove the organic-inorganic-hybrid perovskite nanoparticle layer by a desired pattern to form the organic-inorganic-hybrid perovskite nanoparticle layer on a second light-emitting layer coating substrate. Here, the stamp may include at least one organic polymer selected from the group consisting of polyurethane, polydimethylsiloxane (PDMS), polyethylene oxide (PEO), polystyrene (PS), polycaprolactone (PCL), polyacrylonitrile (PAN), poly(methyl methacrylate) (PMMA), polyimide, poly(vinylidene fluoride) (PVDF), poly(n-vinylcarbazole) (PVK), and polyvinylchloride (PVC).

The step of applying the solution may include the organic-inorganic-hybrid perovskite nanoparticle including the organic-inorganic-hybrid perovskite nanocrystal structure on the light emitting layer coating substrate to form the first thin film of the nanoparticle is repeatedly performed several times to adjust a thickness of the light emitting layer, and before and after the step of forming the first thin film of the nanoparticle, the method may further include a step of forming a second thin film of an organic-inorganic-hybrid perovskite microparticle or organic-inorganic-hybrid perovskite that include the organic-inorganic-hybrid perovskite nanocrystal structure on the light emitting layer coating substrate or the first thin film of the nanoparticle.

Another aspect of the present invention provides a light emitting layer. The light emitting layer includes: a light emitting layer coating substrate; and a light emitting layer disposed on the light emitting layer coating substrate and including the thin film of the nanoparticle, which includes the organic-inorganic-hybrid perovskite nanocrystal structure and is manufactured through the foregoing method.

Here, the first thin film of the nanoparticle may have a multilayer structure, and a second thin film of an organic-inorganic-hybrid perovskite microparticle or organic-inorganic-hybrid perovskite including the organic-inorganic-hybrid perovskite crystal structure may be further disposed between the light emitting layer coating substrate and the first thin film of the nanoparticle or on the first thin film of the nanoparticle.

Further another aspect of the present invention provides a light emitting device. The light emitting device includes: a first electrode disposed on a substrate; a light emitting layer disposed on the first electrode and including the first thin film of the nanoparticle, which includes an organic-inorganic-hybrid perovskite nanocrystal structure and is manufactured through the foregoing method. Here, the light emitting device may further include an exciton buffer layer disposed between the first electrode and the light emitting layer and including a conductive material and a fluorine-based material having surface energy less than that of the conductive material.

Also, the first thin film of the nanoparticle may have a multilayer structure, and a second thin film of an organic-inorganic-hybrid perovskite microparticle or organic-inorganic-hybrid perovskite including the organic-inorganic-hybrid perovskite crystal structure may be further disposed between the first electrode and the first thin film of the nanoparticle or on the first thin film of the nanoparticle.

To achieve the object, another aspect of the present invention provides a method of a light emitting layer. The method of a light emitting layer includes steps of: preparing a light emitting layer coating substrate; and applying a solution including inorganic metal halide perovskite nanoparticles that have an inorganic metal halide perovskite nanocrystal structure on the light emitting layer coating substrate to form a first thin film of a nanoparticle.

Also, the step of forming the first thin film of the nanoparticle may use a solution process.

Also, the solution process may include at least one process selected from the group consisting of spin-coating, bar coating, slot-die coating, Gravure-printing, nozzle printing, ink-jet printing, screen printing, electrohydrodynamic jet printing, and electrospray.

To achieve the object, another aspect of the present invention provides a light emitting layer including: a light emitting layer coating substrate; and a light emitting layer disposed on the light emitting layer coating substrate and including the thin film of the nanoparticle, which includes the inorganic metal halide perovskite nanocrystal structure and is manufactured through the foregoing method.

To achieve the object, another aspect of the present invention provides a photoactive layer including: a coating substrate; and a nanoparticle thin film disposed on the coating member, including the organic-inorganic-hybrid perovskite nanocrystal structure, and manufactured through the foregoing method.

Advantageous Effects

In the light emitting layer for the organic-inorganic-hybrid perovskite or the inorganic metal halide perovskite light emitting device, the method for manufacturing the same, and the organic-inorganic-hybrid perovskite or the inorganic metal halide perovskite light emitting device using the same, the organic-inorganic-hybrid perovskite or inorganic metal halide perovskite having the crystal structure, in which the FCC and the BCC are combined with each other, may be formed in the nanocrystal particle light-emitter, a lamellar structure, in which the organic plane (or the alkali metal plane) and the inorganic plane are alternately stacked, may be formed, and the excitons may be confined in the inorganic plane to implement the high color purity. Also, after the perovskite is manufactured into the nanoparticle, the light emitting layer may be introduced to improve the luminescent efficiency and the luminance of the device.

BRIEF DESCRIPTION OF THE DRAWINGS

FIG. 15 is a schematic view of a nanoparticle according to Manufacturing Example and Comparative Example 1.

MODE FOR CARRYING OUT THE INVENTION

Figure 1:
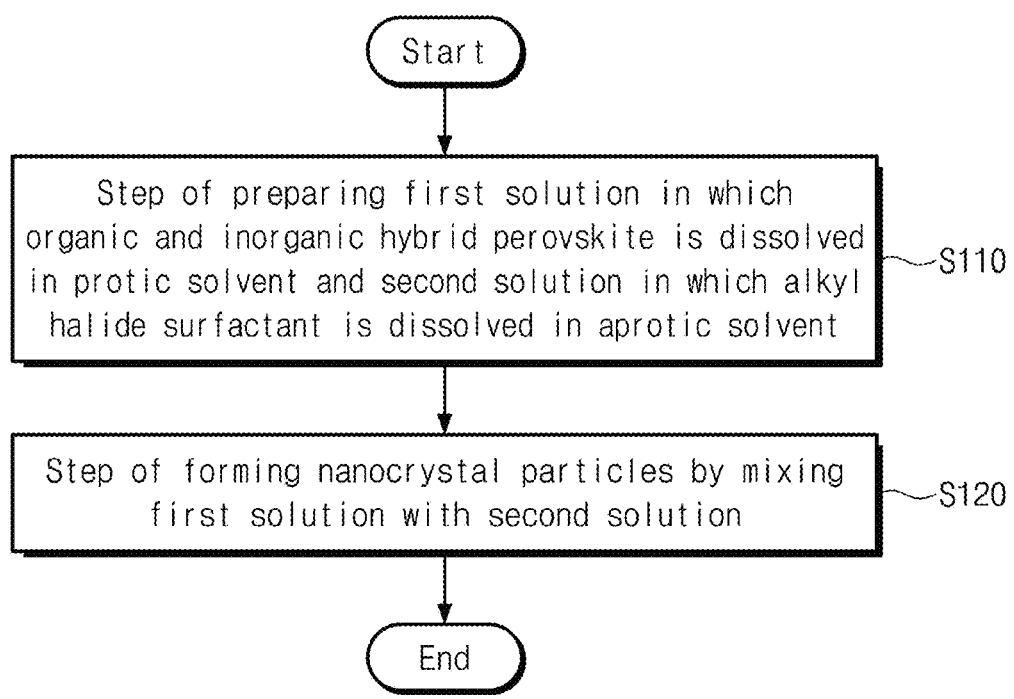
FIG. 1 is a flowchart illustrating a method for manufacturing a solution including an organic-inorganic-hybrid perovskite nanoparticle including an organic-inorganic-hybrid perovskite nanocrystal structure according to an embodiment of the present invention.

Hereinafter, preferred embodiments of the present invention will be described in detail with reference to the accompanying drawings. The present invention may, however, be embodied in different forms and should not be construed as limited to the embodiments set forth herein. Like reference numerals designate like elements throughout the specification.

In this specification, it will be understood that when an element such as a layer or substrate is referred to as being on another element, it can be directly on the other element or intervening elements may also be present. Also, in this specification, directional expressions of the upper side, upper (upper portion), top surface, and the like can be understood as meaning lower side, lower (portion), bottom surface, and the like according to the standard. That is, the expression of spatial direction should be understood in relative direction and should not be construed as meaning absolute direction.

<Light Emitting Layer for Organic-Inorganic-Hybrid Perovskite Light Emitting Device>

A method for manufacturing a light emitting layer for an organic-inorganic-hybrid perovskite light emitting device according to an embodiment of the present invention will be described.

A method for forming the light emitting layer with an inorganic metal halide perovskite nanoparticle instead of the organic-organic hybrid perovskite nanoparticle is the same. Thus, the method for manufacturing the light emitting layer for the organic-organic hybrid perovskite light emitting device will be described as an example.

The method for manufacturing the light emitting layer for the organic-inorganic-hybrid perovskite light emitting device according to an embodiment of the present invention includes a step of preparing a light emitting layer coating substrate and a step of coating with a solution including an organic-inorganic-hybrid perovskite nanoparticle including an organic-inorganic-hybrid perovskite nanocrystal structure on the above-described light emitting layer coating substrate.

First, the light emitting layer coating substrate is prepared. The above-described light emitting layer coating substrate may be a substrate, an electrode, or a semiconductor layer. A substrate, an electrode, or a semiconductor layer, which is capable of being used for the light emitting device, may be used as the above-described substrate, electrode, or semiconductor layer. Also, the light emitting layer coating substrate may have a shape in which the substrate/electrode are successively stacked or a shape in which the substrate/electrode/semiconductor layer are successively stacked. Also, descriptions with respect to the above-described substrate, electrode, or semiconductor layer refer to those with respect to an 'organic-inorganic-hybrid perovskite light emitting device' that will be described later.

FIG. 1 is a flowchart illustrating a method for manufacturing a solution including a colloidal organic-inorganic-hybrid perovskite nanoparticle including an organic-inorganic-hybrid perovskite nanocrystal structure according to an embodiment of the present invention.

Referring to FIG. 1, a method for manufacturing a solution including an organic-inorganic-hybrid perovskite nanocrystal particle including an organic-inorganic-hybrid perovskite nanocrystal structure may include a step (S100) of a first solution in which organic-inorganic-hybrid perovskite is dissolved in a polar solvent and a second solution in which an alkyl halide surfactant is dissolved in a non-polar solvent and a step (200) of mixing the first solution with the second solution to form a nanoparticle.

That is, the organic-inorganic-hybrid perovskite nanocrystalline particle according to the present invention may be manufactured through an inverse nano-emulsion method, or reprecipitation method.

Hereinafter, more specifically,

First, a first solution in which the organic-inorganic-hybrid perovskite is dissolved in a polar solvent and a second solution in which a surfactant is dissolved in a non-polar solvent are prepared (S100).

Here, the polar solvent (aprotic or protic) may include dimethylformamide, gamma butyrolactone, N-methylpyrrolidone, or dimethylsulfoxide, or isopropyl alcohol, but is not limited thereto.

Also, the organic-inorganic-hybrid perovskite may be a material having a 2D crystal structure. For example, the organic-inorganic-hybrid perovskite may be a structure of $ABX_3$, $A_2BX_4$, $ABX_4$, or $A_{n-1}B_nX_{3n+1}$ (where, n is an integer between 2 to 6).

Here, the A is an organic ammonium or inorganic alkali metal material, the B is a metal material, and the X is a halogen element.

For example, the A may be, $(CH_3NH_3)_n$, $((C_xH_{2x+1})_nNH_3)_n(CH_3NH_3)_n$, $R(NH_2)_2$ (R=alkyl), $(C_nH_{2n+1}NH_3)_n$, $CF_3NH_3$, $(CF_3NH_3)_n$, $((C_xF_{2x+1})_nNH_3)_n(CF_3NH_3)_n$, $((C_xF_{2x+1})_nNH_3)_n$, $(C_nF_{2n+1}NH_3)_n$, $(CH(NH_2)_2)$, $C_xH_{2x+1}NH_3$, Cs, Rb, K (where n is an integer greater than 1, and x is an integer greater than 1), or a derivative thereof. Also, the B may be a divalent transition metal, an organic material, an ammonium, a rare earth metal, an alkaline earth metal, Pb, Sn, Ge, Ga, In, Al, Sb, Bi, Po, or a combination thereof. Here, the rare earth metal may be a divalent rare earth metal. For example, the rare earth metal may be Ge, Sn, Pb, Eu, or Yb. Also, the alkali earth metal may be, for example, Ca or Sr. Also, the X may be Cl, Br, I, or a combination thereof.

The perovskite may be prepared by combining the AX with $BX_2$ at a predetermined ratio. That is, the first solution may be formed by dissolving the AX and $BX_2$ in the polar solvent at a predetermined ratio. For example, the AX and $BX_2$ may be dissolved in the polar solvent at a ratio of 2:1 to prepare the first solution in which the $A_2BX_3$ organic-inorganic-hybrid perovskite is dissolved.

Also, the non-polar solvent may include dichloroethylene, trichlorethylene, chloroform, chlorobenzene, dichlorobenzene, styrene, xylene, toluene, or cyclohexene, but is not limited thereto.

Also, the alkyl halide surfactant may have a structure of alkyl-X. Here, the halogen element corresponding to the X may include Cl, Br, or I. Also, the alkyl structure may include acyclic alkyl having a structure of $C_nH_{2n+1}$, primary alcohol having a structure such as $C_nH_{2n+1}OH$, secondary alcohol, tertiary alcohol, alkylamine having a structure of alkyl-N (e.g., hexadecyl amine, 9-Octadecenylamine 1-Amino-9-octadecene $(C_{19}H_{37}N)$, p-substituted aniline, phenyl ammonium, and fluorine ammonium, but is not limited thereto.

A carboxylic acid (COOH) surfactant may be used instead of the alkyl halide surfactant.

For example, the surfactant may include a carboxylic acid such as a 4,4'-Azobis(4-cyanovaleric acid), an acetic acid, a 5-aminosalicylic acid, an acrylic acid, an L-aspentic acid, a 6-bromohexanoic acid, a bromoacetic acid, a dichloro acetic acid, an ethylenediaminetetraacetic acid, an isobutyric acid, an itaconic acid, a maleic acid, an r-maleimidobutyric acid, an L-malic acid, a 4-Nitrobenzoic acid, a 1-pyrenecarboxylic acid, or an oleic acid, but is not limited thereto.

Next, the first solution may be mixed with the second solution to form the nanoparticle. (S200).

In the step of mixing the first solution with the second solution to form the nanoparticle, it is preferable to mix the first solution by dropping into the second solution in drops. Also, the first solution may be stirred. For example, the second solution in which the organic-inorganic-hybrid perovskite (OIP) is dissolved may be slowly added dropwise into the second solution in which the alkyl halide surfactant that is strongly stirred is dissolved to synthesize the nanoparticle.

In this case, when the first solution drops are mixed with the second solution, the organic-inorganic-hybrid perovskite (OIP) is precipitated from the second solution due to a difference in solubility. Also, the organic-inorganic-hybrid perovskite (OIP) precipitated from the second solution generates an organic-inorganic-hybrid perovskite nanocrystal (OIP-NC) that is well dispersed while stabilizing a surface thereof by the alkyl halide surfactant. Thus, a solution including the organic-inorganic hybrid metal halide perovskite colloidal nanoparticle and the plurality of alkyl halide organic or inorganic ligands, inorganic binary compounds or combination thereof surrounding the organic-inorganic-hybrid metal halide perovskite nanocrystal may be prepared.

The solution including the organic-inorganic-hybrid metal halide perovskite colloidal nanoparticles is applied on the light emitting layer coating substrate to form a first thin film of nanoparticles that is a light emitting layer.

Figure 2:
FIG. 2 is a cross-sectional view of a light emitting layer according to an embodiment of the present invention.

FIG. 2 is a cross-sectional view of a light emitting layer according to an embodiment of the present invention.

Referring to FIG. 2, it is seen that the light emitting layer having the form of the first thin film 200a of the nanoparticle on the light emitting layer coating substrate 100.

A step of forming the first thin film of the nanoparticle may use a solution process. When the solution process is used, the light emitting layer may be uniformly formed on the light emitting layer coating substrate.

The above-described solution process may include at least one process selected from the group consisting of spin-coating, bar coating, slot-die coating, gravure-printing, nozzle printing, ink-jet printing, screen printing, electrohydrodynamic jet printing, and electrospray.

Figure 3:
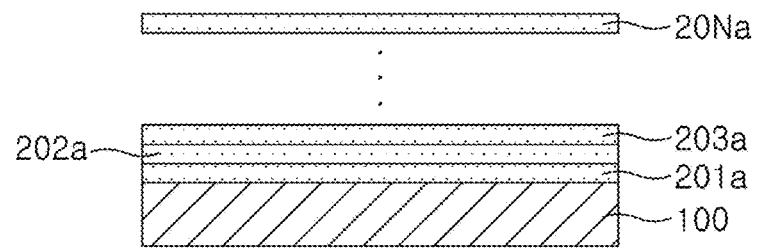
FIG. 3 is a sectional view of a light emitting layer according to another embodiment of the present invention.

FIG. 3 is a sectional view of a light emitting layer according to another embodiment of the present invention.

The step of applying the solution including the organic-inorganic-hybrid perovskite nanoparticle including the organic-inorganic-hybrid perovskite nanocrystal structure on the light emitting layer coating substrate to form the first thin film of the nanoparticle may be repeatedly performed several times to adjust a thickness of the light emitting layer.

Referring to FIG. 3, the first thin film of the nanoparticle may have a multilayer (N layers) structure.

FIGS. 4a to 4d are cross-sectional views of a light emitting layer according to further another embodiment of the present invention.

Before or after the step of forming the first thin film of the nanoparticle, a step of forming a second thin film of an organic-inorganic-hybrid perovskite microparticle or the organic-inorganic-hybrid perovskite including the organic-inorganic-hybrid perovskite nanocrystal structure on the light emitting layer coating substrate or the first thin film of the nanoparticle may be further performed.

Here, the second thin film of the organic-inorganic-hybrid perovskite microparticle or the organic-inorganic-hybrid perovskite may be formed by applying only the first solution, unlike the process in which the first solution and the second solution are mixed to manufacture the solution including the organic-inorganic-hybrid perovskite nanoparticle. In this case, unlike the solution including the organic-inorganic-hybrid perovskite nanoparticle including the above-described organic-inorganic-hybrid perovskite nanocrystal structure, the second thin film of the organic-inorganic-hybrid perovskite includes the organic-inorganic-hybrid perovskite microparticle having a micro range or the organic-inorganic-hybrid perovskite crystal structure having several nano to several micro ranges.

Figure 4A:
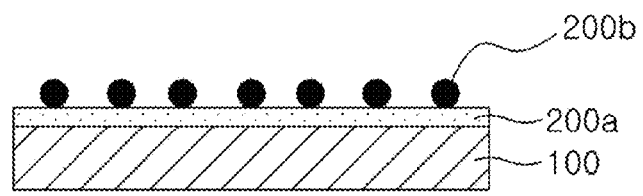
FIGS. 4a to 4d are cross-sectional views of a light emitting layer according to further another embodiment of the present invention.
Figure 4B:
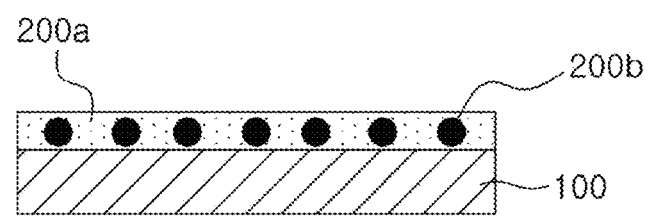
Figure 4C:
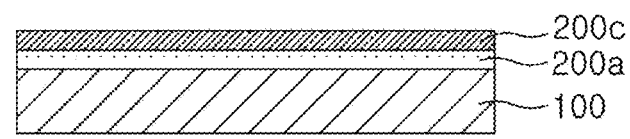
Figure 4D:
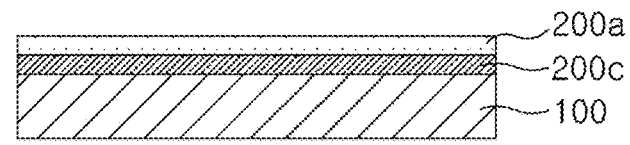

In this case, a shape in which the above-described organic-inorganic-hybrid perovskite microparticle 200b is disposed on the first thin film 200a of the nanoparticle as illustrated in FIG. 4(a), a shape in which the above-described first thin film 200a of the nanoparticle is formed on the above-described organic-inorganic-hybrid perovskite microparticle 200b as illustrated in FIG. 4(b), a shape in which the above-described second thin film 200c of the organic-inorganic-hybrid perovskite is disposed on the above-described first thin film 200a of the nanoparticle as illustrated in FIG. 4(c), or a shape in which the above-described first thin film 200a of the nanoparticle is formed on the above-described second thin film 200c of the organic-inorganic-hybrid perovskite as illustrated in FIG. 4(d) may be formed on the above-described light emitting layer coating substrate 100.

The organic-inorganic-hybrid perovskite microparticle may have various shapes such as a spherical shape and a polygonal shape.

Also, the first thin film of the nanoparticle may range from 1 nm to 1 μm, and surface roughness may range of 0.1 nm to 50 nm.

Here, the organic-inorganic-hybrid perovskite nanocrystal particle may have a spherical, cylindrical, cylindroid, polyprism or two-dimensional (lamellar, plate) shape.

Also, the organic-inorganic-hybrid perovskite nanocrystal particle may have bandgap energy of 1 eV to 5 eV.

Also, the organic-inorganic-hybrid perovskite nanoparticle may have an emission wavelength of 200 nm to 1300 nm.

The organic-inorganic-hybrid perovskite nanocrystal may have a size that is controllable by adjusting a length or a shape of the alkyl halide surfactant. For example, the adjustment of the shape may be controlled through the surfactant having a linear, tapered, or inverted triangular shape.

The generated organic-inorganic-hybrid perovskite nanocrystal may have a size of 1 nm to 900 nm. If the organic-inorganic-hybrid perovskite nanocrystal has a size exceeding 900 nm, it is a fundamental problem in which the large non-radiative decay of the excitons can occur at room temperature by the thermal ionization and the delocalization of the charge carriers, and the exciton is separated as free charge carriers and then annihilated.

Figure 5:
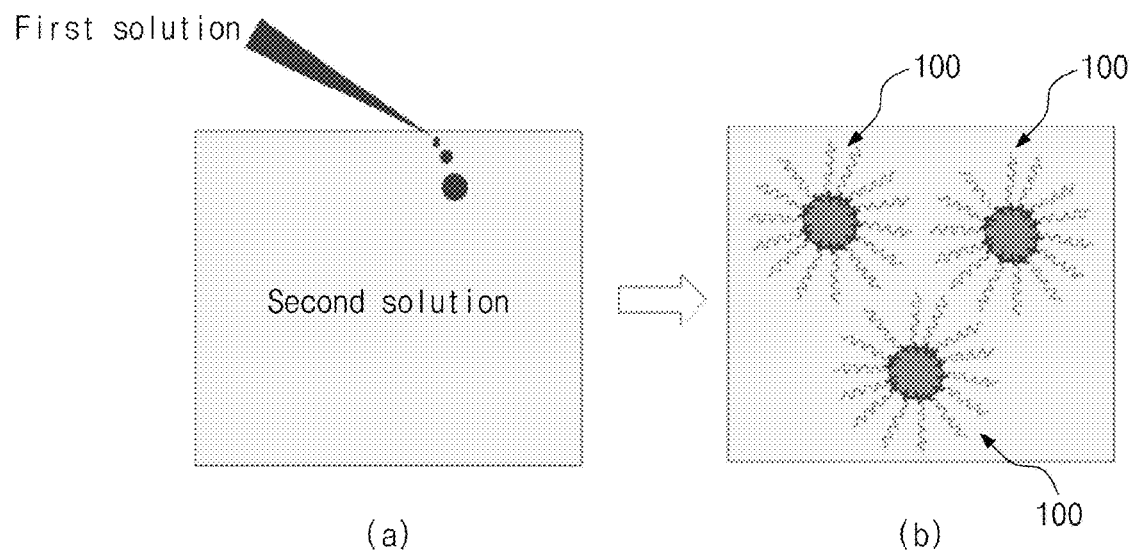
FIG. 5 is a schematic view illustrating a method for manufacturing the organic-inorganic-hybrid perovskite nanocrystal particle through an inverse nano-emulsion method, or reprecipitation method, or hot injection method according to an embodiment of the present invention.

FIG. 5 is a schematic view illustrating a method for manufacturing the organic-inorganic-hybrid perovskite nanocrystal particle through an inverse nano-emulsion method, reprecipitation method, or hot injection method according to an embodiment of the present invention.

Referring to FIG. 5(a), the first solution in which the organic-inorganic-hybrid perovskite is dissolved in the polar solvent is added drop wise into the second solution in which the alkyl halide surfactant is dissolved in the non-polar solvent.

Here, the polar solvent (aprotic or protic) may include dimethylformamide, gamma butyrolactone, N-methylpyrrolidone, or dimethylsulfoxide, or isopropyl alcohol, but is not limited thereto.

Here, the organic-inorganic-hybrid perovskite may be a structure of $ABX_3$, $A_2BX_4$, $ABX_4$, or $A_{n-1}B_nX_{3n+1}$ (where, n is an integer between 2 to 6). Here, the A is an organic ammonium or inorganic alkali metal material, the B is a metal material, and the X is a halogen element.

For example, the A may be $(CH_3NH_3)_n$, $((C_xH_{2x+1})_nNH_3)_n(CH_3NH_3)_n$, $R(NH_2)_2$ (R=alkyl), $(C_nH_{2n+1}NH_3)_n$, $CF_3NH_3$, $(CF_3NH_3)_n$, $((C_xF_{2x+1})_nNH_3)_n(CF_3NH_3)_n$, $((C_xF_{2x+1})_nNH_3)_n$, $(C_nF_{2n+1}NH_3)_n$, $(CH(NH_2)_2)$, $C_xH_{2x+1}$ (NH$_3$), Cs, Rb, K (where n is an integer greater than 1, and x is an integer greater than 1), or a derivative thereof. Also, the B may be a divalent transition metal, an organic material, an ammonium, a rare earth metal, an alkaline earth metal, Pb, Sn, Ge, Ga, In, Al, Sb, Bi, Po, or a combination thereof. Here, the rare earth metal may be a divalent rare earth metal, for example, Ge, Sn, Pb, Eu, or Yb. Also, the alkali earth metal may be, for example, Ca or Sr. Also, the X may be Cl, Br, I, or a combination thereof.

The perovskite structure may be formed through a combination of AX and BX$_2$ with different AX:BX$_2$ ratios. For example, the AX and BX$_2$ may be dissolved in the polar solvent at a ratio of 2:1 to prepare the first solution in which the A$_2$BX$_3$ organic-inorganic-hybrid perovskite is dissolved.

When the A is CH$_3$NH$_3$, and the X is Br as an example of the AX synthesis, CH$_3$NH2 (methylamine) and HBr (hydroiodic acid) may be dissolved under a nitrogen atmosphere to obtain CH$_3$NH$_3$Br through evaporation of the solvent.

Referring to FIG. 5(b), when the first solution is added to the second solution, the organic-inorganic-hybrid perovskite is precipitated from the second solution due to a difference in solubility. A surface of the precipitated organic-inorganic-hybrid perovskite is surrounded by the alkyl halide surfactant and thus stabilized to generate an organic-inorganic-hybrid perovskite nanoparticle 100 including the organic-inorganic-hybrid perovskite nanocrystal structure that is well dispersed. Here, the surface of the organic-inorganic-hybrid perovskite nanoparticle is surrounded by the organic ligands that include alkyl halide, inorganic binary compounds or combination thereof.

Thereafter, the polar solvent including the organic-inorganic-hybrid perovskite nanoparticle 100 that is dispersed in the non-polar solvent, in which the alkyl halide surfactant is dissolved, may be heated and thus selectively evaporated, or a co-solvent, in which all the polar and non-polar solvents are capable of being dissolved, may be added to selectively extract the polar solvent including the nanoparticle from the non-polar solvent, thereby obtaining the organic-inorganic-hybrid perovskite nanoparticle.

The organic-inorganic-hybrid perovskite nanoparticle according to an embodiment of the present invention will be described.

Figure 6:
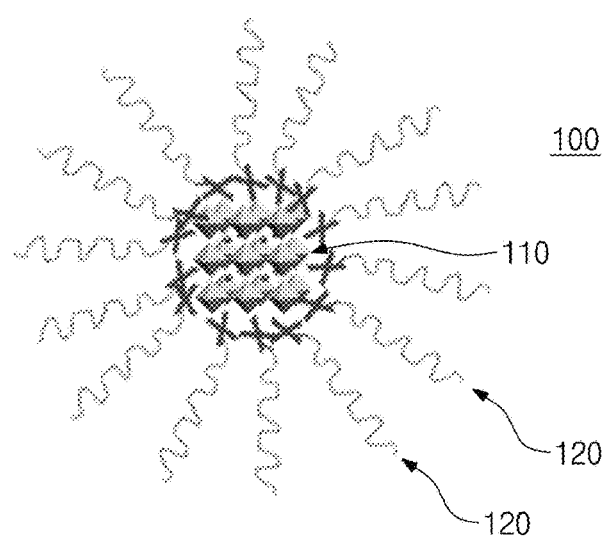
FIG. 6 is a schematic view of an organic-inorganic-hybrid perovskite nanocrystalline particle light-emitter and an inorganic metal halide perovskite nanocrystal particle light-emitter according to an embodiment of the present invention.

FIG. 6 is a schematic view of the perovskite nanoparticle according to an embodiment of the present invention.

Here, FIG. 6 illustrates the organic-inorganic-hybrid perovskite nanocrystal particle. If the organic-inorganic-hybrid perovskite of FIG. 6 is changed into the inorganic metal halide perovskite, since the inorganic metal halide perovskite nanocrystal particle is provided, their descriptions are the same.

Referring to FIG. 6, the light-emitter according to an embodiment of the present invention may include a 2D organic-inorganic-hybrid perovskite nanocrystal 110 having a lamellar structure, in which an organic plane (or an alkali metal plane) and an inorganic plane are alternately stacked, as an organic-inorganic-hybrid perovskite (or inorganic metal halide perovskite) nanoparticle.

The 2D organic-inorganic-hybrid perovskite may include a structure of ABX$_3$, A$_2$BX$_4$, ABX$_4$, or A$_{n-1}$B$_n$X$_{3n+1}$ (where, n is an integer between 2 to 6). Here, the A is an organic ammonium or inorganic alkali metal material, the B is a metal material, and the X is a halogen element. For example, the A may be (CH$_3$NH$_3$)$_n$, ((C$_x$H$_{2x+1}$)$_n$NH$_3$)$_n$(CH$_3$NH$_3$)$_n$, R(NH$_2$)$_n$ (R=alkyl), (C$_n$H$_{2n+1}$NH$_3$)$_n$, CF$_3$NH$_3$, (CF$_3$NH$_3$)$_n$, ((C$_x$F$_{2x+1}$)$_n$NH$_3$)$_n$(CF$_3$NH$_3$)$_n$, ((C$_x$F$_{2x+1}$)$_n$NH$_3$)$_n$, (C$_n$F$_{2n+1}$NH$_3$)$_n$, (CH(NH$_2$)$_2$), C$_x$H$_{2x+1}$(CNH$_3$), Cs, Rb, K (where n is an integer greater than 1, and x is an integer greater than 1), or a combination thereof. Also, the B may be a divalent transition metal, organic material, an ammonium, a rare earth metal, an alkaline earth metal, Pb, Sn, Ge, Ga, In, Al, Sb, Bi, Po, or a combination thereof. Here, the rare earth metal may be a divalent rare earth metal, for example, Ge, Sn, Pb, Eu, or Yb. Also, the alkali earth metal may be, for example, Ca or Sr. Also, the X may be Cl, Br, I, or a combination thereof.

The organic-inorganic-hybrid perovskite nanoparticle 100 according to the present invention may further include a plurality of organic or inorganic ligands 120, inorganic binary compounds or combination thereof surrounding the above-described organic-inorganic-hybrid or metal halide perovskite nanocrystal 110. Each of the organic ligands 120 may be a material used as the surfactant and include alkyl halide. Thus, as described above, the alkyl halide used as the surfactant for stabilizing the surface of the precipitated organic-inorganic-hybrid perovskite may become the organic ligand surrounding the surface of the organic-inorganic-hybrid metal halide perovskite nanocrystal.

If the alkyl halide surfactant has a short length, the size of formed nanocrystals is increased to exceed 900 nm. In this case, the light emission of the exciton may not occur by thermal ionization and the delocalization of the charge carrier in the large nanocrystal, and the exciton may be separated as the free charge and then annihilated.

That is, the size of the formed organic-inorganic-hybrid perovskite nanocrystal is inversely proportional to the length of the alkyl halide surfactant used for forming the nanocrystal.

Thus, the size of the organic-inorganic-hybrid perovskite nanocrystal formed by using the alkyl halide having a predetermined length or more as the surfactant may be controlled to a predetermined size or less. For example, octadecyl-ammonium bromide may be uses as the alkyl halide surfactant to form the organic-inorganic-hybrid perovskite nanocrystal having a size of a 900 nm or less.

Also, the inorganic metal halide perovskite having the 2D crystal structure may be a structure of A$_2$BX$_4$, ABX$_4$, or A$_{n-1}$Pb$_n$X$_{3n+1}$ (where, n is an integer between 2 to 6).

The A may be an alkali metal, the B may be a divalent transition metal, a rare earth metal, an alkali earth metal, Pb, Sn, Ge, Ga, In, Al, Sb, Bi, Po, or a combination thereof, and the X may be Cl, Br, I, or a combination thereof. Here, the rare earth metal may be, for example, Ge, Sn, Pb, Eu, or Yb. Also, the alkali earth metal may be, for example, Ca or Sr.

The inorganic metal halide perovskite nanocrystal particle having the 2D structure according to the present invention may further include a plurality of organic or inorganic ligands surrounding the above-described inorganic metal halide perovskite nanocrystal structure. Each of the organic ligands may include alkyl halide.

Figure 7:
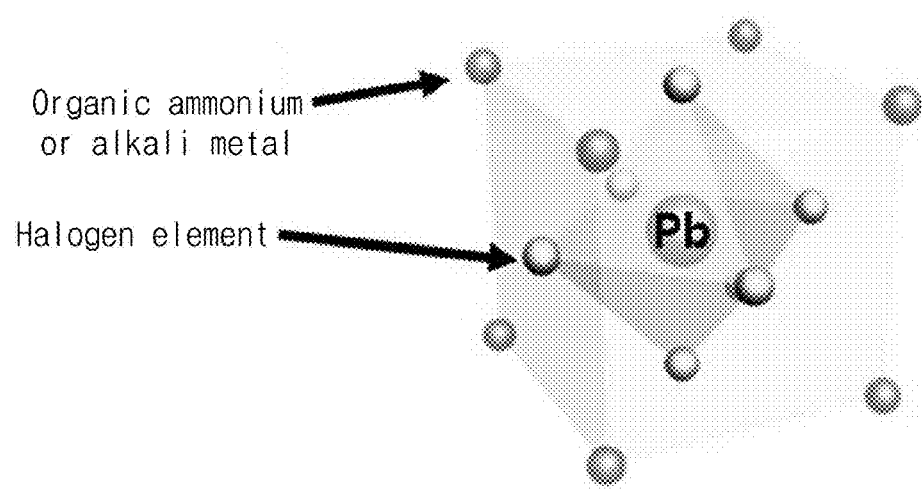
FIG. 7 is a schematic view of a perovskite nanocrystal structure according to an embodiment of the present invention.

FIG. 7 is a schematic view of a perovskite nanocrystal structure according to an embodiment of the present invention.

FIG. 7 illustrates both structures of an organic-inorganic-hybrid perovskite nanocrystal and an inorganic metal halide perovskite nanocrystal.

Referring to FIG. 7, it is seen that the organic-inorganic-hybrid perovskite (or the inorganic metal halide perovskite) nanocrystal structure according to an embodiment of the present invention includes an organic ammonium (or alkali metal) and halides.

Formation of Light Emitting Layer Through Spin-Assembly Process

Figure 8:
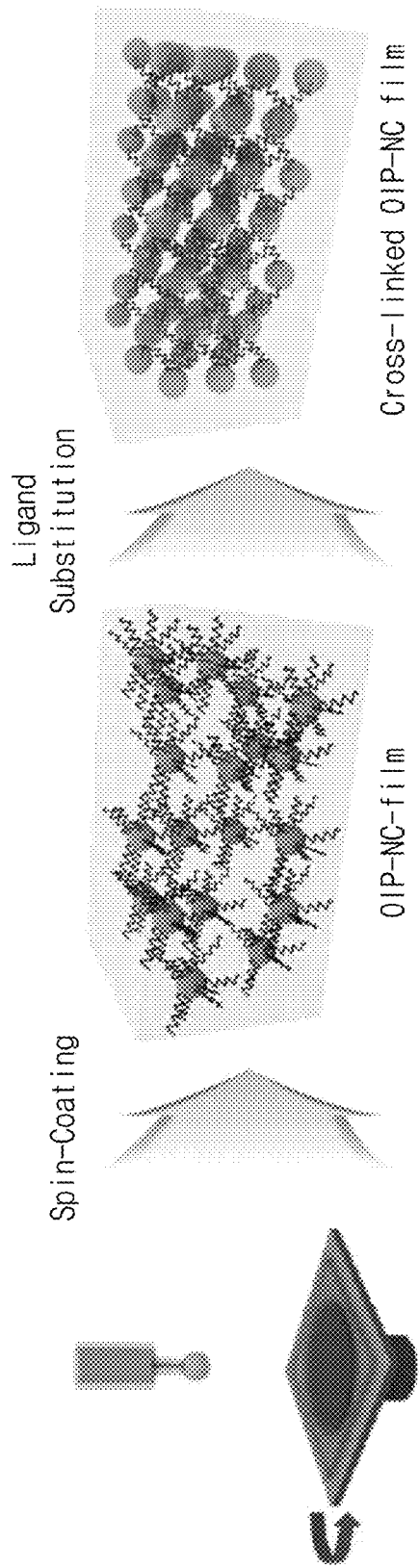
FIG. 8 is a schematic view illustrating a process of forming a light emitting layer through a spin-assembly process according to an embodiment of the present invention.

FIG. 8 is a schematic view illustrating a process of forming a light emitting layer through a spin-assembly process according to an embodiment of the present invention.

Referring to FIG. 8, an anchoring solution and an organic-inorganic-hybrid perovskite nanoparticle solution including the organic-inorganic-hybrid perovskite nanocrystal structure are prepared.

The above-described anchoring solution is a solution including a resin giving adhesion having an anchoring effect. For example, 3-mercaptopropionic acid ethanolic solution may be used. It is preferable that the above-described anchoring solution has a concentration of 7 wt % to 12 wt %.

Then, the anchoring solution may be applied on the above-described light emitting layer coating substrate to form an anchoring agent layer.

Here, it is preferable that a coating rate ranges from 100 rpm to 5000 rpm, and a coating time ranges from 15 seconds to 150 seconds. When the coating rate is less than 1000 rpm, or the coating time is less than 15 seconds, the thin film may be non-uniform, and the solvent may not completely evaporated.

Then, the organic-inorganic-hybrid perovskite nanoparticle solution is applied to the anchoring agent layer to form an anchored light emitting layer. As described above, when the anchored light emitting layer is formed by using the anchoring solution, a denser nanocrystal layer may be formed.

Then, a crosslinking agent layer may be formed on the anchored light emitting layer. When the crosslinking agent is formed, a denser perovskite nanocrystal layer may be formed. Thus, the ligand may be reduced in length, and charge injection into the nanocrystal may be smoother to improve luminescent efficiency and luminance of the light emitting device.

It is preferable that the crosslinking agent is a crosslinking agent having an X—R—X structure, for example, 1,2-ethanedithiol. After the crosslinking agent is mixed with a soluble solvent to perform the spin-coating.

Here, the step of applying the organic-inorganic-hybrid perovskite nanoparticle solution and the step of forming the crosslinking layer on the layer coated with the organic-inorganic-hybrid perovskite nanoparticle solution may be repeatedly alternately performed to adjust a thickness of the light emitting layer.

Here, it is preferable that a coating rate ranges from 100 rpm to 5000 rpm, and a coating time ranges from 15 seconds to 150 seconds. When the coating rate is less than 1000 rpm, or the coating time is less than 15 seconds, the thin film may be non-uniform, and the solvent may not completely evaporated.

Formation of Light Emitting Layer Through Floating Process

Figure 9:
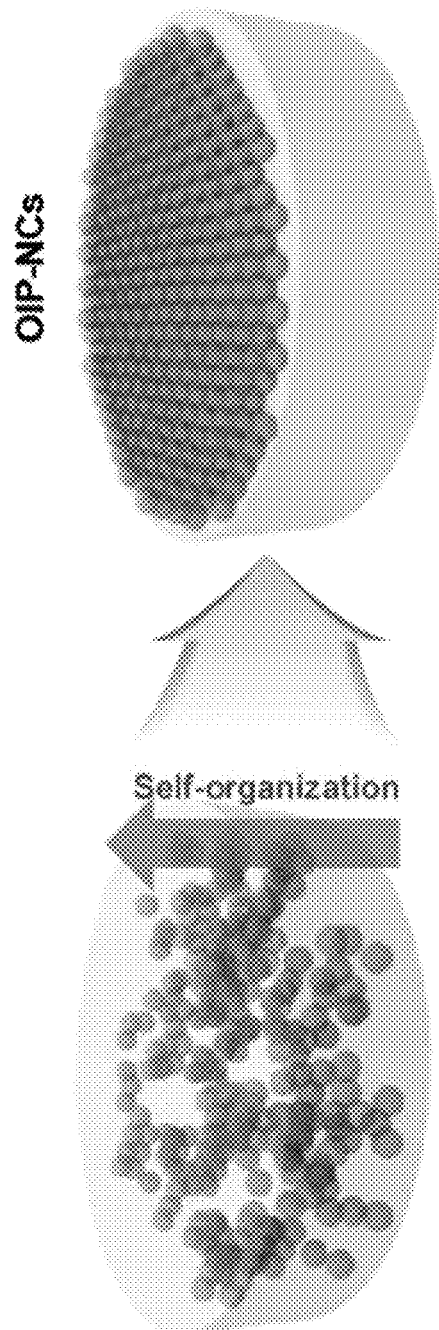
FIG. 9 is a schematic view illustrating a process of forming a light emitting layer through a floating process according to an embodiment of the present invention.

FIG. 9 is a schematic view illustrating a process of forming a light emitting layer through a floating process according to an embodiment of the present invention.

Referring to FIG. 9, a solution including trioctylphosphine (TOP) and trioctylphosphine oxide (TOPO) is added to the solution including the organic-inorganic-hybrid perovskite nanoparticle. As the solution including the TOP and TOPO is added, the ligand of the organic perovskite nanoparticle may be substituted with the TOP and the TOPO.

Then, a solution including a triphenyl diamine (TPD) compound is added to the solution including the organic-inorganic-hybrid perovskite nanoparticle in which the ligand is substituted with the TOP and TOPO. For example, the TPD compound may be N,N'-diphenyl-N,N'-bis(3-methylphenyl)-(1,1'-biphenyl)-4,4'diamine.

The solution including the organic-inorganic-hybrid perovskite nanoparticle in which the ligand is substituted with the TOP and TOPO and the solution including the TPD compound are mixed at a weight ratio of 100:3 to 100:7 to manufacture a TPD-organic-inorganic-hybrid perovskite nanoparticle solution.

Then, the TPD-organic-inorganic-hybrid perovskite nanoparticle solution is applied on the light emitting layer coating substrate to form the light emitting layer for the organic-inorganic-hybrid perovskite light emitting device. Here, the light emitting layer may be self-organized in a shape in which the organic semiconductor layer and the organic-inorganic-hybrid perovskite nanoparticle are successively stacked on the light emitting layer coating substrate to simplify the process.

Here, it is preferable that a coating rate ranges from 1000 rpm to 5000 rpm, and a coating time ranges from 15 seconds to 150 seconds. When the spin coating rate is less than 1000 rpm, or the coating time is less than 15 seconds, the thin film may be non-uniform, and the solvent may not completely evaporated.

Since the light emitting layer is formed through the floating process, an occurrence of pinhole defects may be removed to allow the charge injection into the nanocrystal to be smoother. Thus, the efficiency and the luminance of the light emitting device may be improved. Also, the perovskite nanocrystal may be adjusted in concentration within the organic semiconductor/perovskite nanocrystal mixing solution to adjust the first thin film of the nanoparticle without performing the spin-coating several times.

Formation of Light Emitting Layer Through Dry Contact Printing Process

Figure 10:
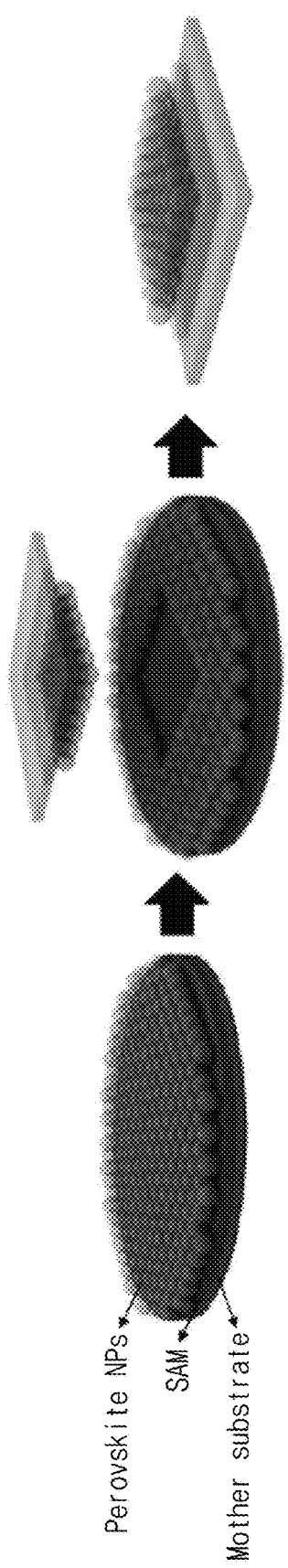
FIG. 10 is a schematic view illustrating a process of forming a light emitting layer through a dry contact printing process according to an embodiment of the present invention.

FIG. 10 is a schematic view illustrating a process of forming a light emitting layer through a dry contact printing process according to an embodiment of the present invention.

Referring to FIG. 10, a self-assembly monolayer may be formed on the light emitting layer coating substrate. Here, a substrate made of a silicon material may be used as the light emitting layer coating substrate. In detail, an ODTS-treated wafer in which a Si native wafer is dipped in an octadecyltrichlorosilane (ODTS) solution may be used.

Then, the solution including the organic-inorganic-hybrid perovskite nanoparticle is applied to the self-assembly monolayer to form an organic-inorganic-hybrid perovskite nanoparticle layer. Finally, a stamp may come into contact with the organic-inorganic-hybrid perovskite nanoparticle layer to remove the organic-inorganic-hybrid perovskite nanoparticle layer by a desired pattern to form the organic-inorganic-hybrid perovskite nanoparticle layer on a second light emitting layer coating substrate.

The stamp may include at least one organic polymer selected from the group consisting of polyurethane), polydimethylsiloxane (PDMS), polyethylene oxide (PEO), polystyrene (PS), polycaprolactone (PCL), polyacrylonitrile (PAN), poly(methyl methacrylate) (PMMA), polyimide, poly(vinylidene fluoride) (PVDF), poly(n-vinylcarbazole) (PVK), and polyvinylchloride (PVC). The stamp may be manufactured by curing a stamp including the above-described materials on the silicon wafer.

As described above, when the dry contact printing process is used, the organic-inorganic-hybrid perovskite nanoparticle layer may be formed through the stamping process to solve the difficulty of substrate sensitivity, large-area assembly, and layer-by-layer stacking processes, which are problems in the existing wet process.

Figure 11:
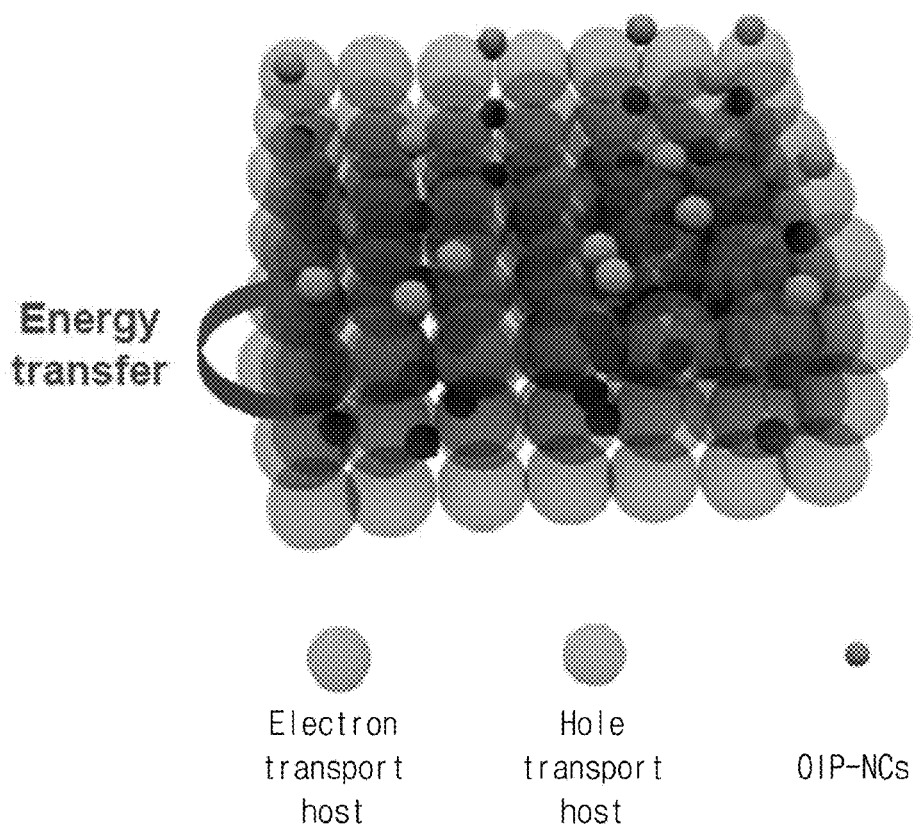
FIG. 11 is a schematic view illustrating a process of forming a light emitting layer through an organic-inorganic-hybrid perovskite-organic composite formation process according to an embodiment of the present invention.

Formation of Light Emitting Layer Through Organic-Inorganic-Hybrid Perovskite-Organic Composite Formation Process FIG. 11 is a schematic view illustrating a process of forming a light emitting layer through a formation process of a composite (or blend) including an organic-inorganic-hybrid perovskite and an organic materialaccording to an embodiment of the present invention.

Referring to FIG. 11, in the step of forming the first thin film of the nanoparticle, the organic semiconductor is mixed with the solution including the organic-inorganic-hybrid perovskite nanoparticle to manufacture an organic-inorganic-hybrid perovskite-organic semiconductor solution.

The organic semiconductor may be at least one selected from the group consisting of tris(8-quinolinolate)aluminum (Alq3), TAZ, TPQ1, TPQ2, bphen(4,7-diphenyl-1,10-phenanthroline), BCP, BeBq2, BAlq, 4,4'-N,N'-dicarbazole-biphenyl) (CBP), 9,10-di(naphthalen-2-yl) anthracene (ADN), tris(N-carbazolyl)triphenylamine) (TCTA), 1,3,5-tris(N-phenylbenzimidazole-2-yl)benzene (TPBI), 3-tert-butyl-9,10-di(naphth-2-yl) anthracene (TBADN), and E3, but is not limited thereto.

Then, the organic-inorganic-hybrid perovskite-organic semiconductor solution is applied to form the light emitting layer. Here, it is preferable that a coating rate ranges from 1000 rpm to 5000 rpm, and a coating time ranges from 15 seconds to 150 seconds. When the spin coating rate is less than 1000 rpm, or the coating time is less than 15 seconds, the thin film may be non-uniform, and the solvent may not completely evaporated.

Thus, in the light emitting layer of the present invention, the organic-inorganic-hybrid perovskite nanoparticle including the organic-inorganic-hybrid perovskite nanocrystal structure is applied to the light emitting layer coating substrate to form the first thin film of the nanoparticle. Thus, the organic-inorganic-hybrid perovskite having the crystal structure, in which the FCC and the BCC are combined with each other, may be formed in the nanocrystal particle light-emitter to form a lamellar structure in which the organic plane and the inorganic plate are alternately stacked, and also, the excitons may be confined in the inorganic plane to implement the high color purity. Also, after the perovskite is manufactured into the nanoparticle, the light emitting layer may be introduced to improve the luminescent efficiency and the luminance of the device.

As described above, when the light emitting layer is formed through the formation process of a composite of an organic-inorganic-hybrid perovskite andan organic host, exciton-exciton annihilation that occurs because the nanocrystal is densely disposed in the existing perovskite nanocrystal layer may be prevented. Also, since an organic host or co-host having a bipolar property is used, a recombination zone may increases to prevent the exciton-exciton annihilation from occurring. Thus, roll-off occurring when the perovskite nanocrystal light emitting device is driven with high luminance may be reduced.

<Organic-Inorganic-Hybrid Perovskite Light Emitting Device>

FIGS. 12a to 12d are cross-sectional views illustrating a method for manufacturing a light emitting device according to an embodiment of the present invention.

Figure 12A:
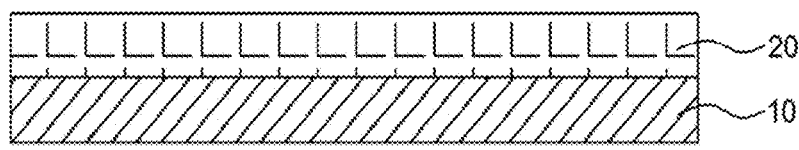
FIGS. 12a to 12d are cross-sectional views illustrating a method for manufacturing a light emitting device according to an embodiment of the present invention.

Referring to FIG. 12a, a first electrode 20 is formed on a substrate 10.

The substrate 10 becomes a support of the organic light emitting device and is made of a transparent material. Also, the substrate may be made of a flexible material and a hard material, but it is preferable that the substrate is made of the flexible material. Particularly, the material of the substrate 10, which has the transparent and flexible properties, may be PET, PS, PI, PVC, PVP, or PE.

The first electrode 20 is an electrode into which a hole is injected and made of a conductive material. The first electrode 20 may be made of metal oxide, preferably, transparent conductive metal oxide. For example, the transparent conductive metal oxide may be ITO, AZO(Al-doped ZnO), GZO(Ga-doped ZnO), IGZO(In,Ga-dpoed ZnO), MZO(Mg-doped ZnO), Mo-doped ZnO, Al-doped MgO, Ga-doped MgO, F-doped $SnO_2$, Nb-dpoed $TiO_2$, or $CuAlO_2$.

A process of depositing the first electrode 20 may include physical vapor deposition (PVD), chemical vapor deposition (CVD), sputtering, pulsed laser deposition (PLD), thermal evaporation, electron beam evaporation, atomic layer deposition (ALD), and molecular beam epitaxy (MBE).

Figure 12B:
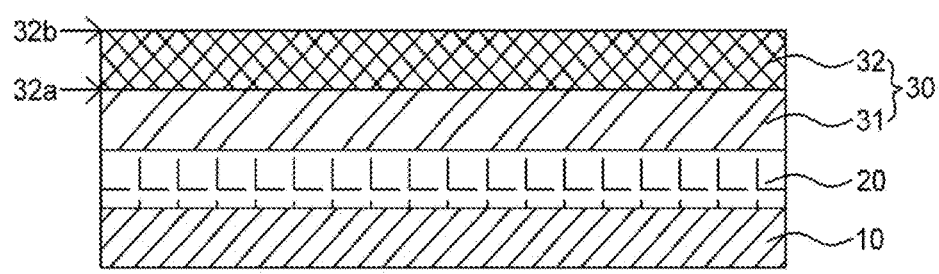

Referring to FIG. 12b, an exciton buffer layer 30 including a conductive material and a fluoric material having surface energy less than that of the conductive material may be formed on the first electrode 20.

Here, the exciton buffer layer 30 may have a shape in which a conductive layer 31 including the conductive material and a surface buffer layer 32 including the fluoric material having the surface energy less than that of the conductive material are successively stacked. The conductive layer 31 includes a conductive material. Also, it is preferable that the conductive layer 31 does not include the fluoric material.

The conductive material may include at least one selected from the group consisting of a conductive polymer, metallic carbon nanotube, graphene, reduced graphene oxide, metal nanowire, semiconductor nanowire, metal grid, metal nano dots, and conductive oxide.

The conductive polymer may include polythiophene, polyaniline, polypyrrole, polystyrene, sulfonated polystyrene, poly(3,4-ethylenedioxythiophene), self-doped conductive polymers, derivatives thereof, or a combination thereof. The derivatives may further include various sulfonic acids.

For example, the conductive polymer may include at least one selected from the group consisting of polyaniline/Dodecylbenzenesulfonic acid (Pani:DBSA), poly(3,4-ethylenedioxythiophene)/poly(4-styrenesulfonate) (PEDOT:PSS), polyaniline/camphor sulfonicacid (Pani:CSA), and polyaniline)/poly(4-styrenesulfonate) (PANI:PSS), but is not limited thereto.

For example, the conductive polymer may include polyaniline/dodecylbenzenesulfonic acid (Pani:DBSA) (see following Chemical Formula), poly(3,4-ethylenedioxythiophene)/poly(4-styrenesulfonate) (PEDOT:PSS) (see following Chemical Formula), polyaniline/camphor sulfonicacid (Pani:CSA) (see following Chemical Formula), or polyaniline/poly(4-styrenesulfonate) (PANI:PSS), but is not limited thereto.

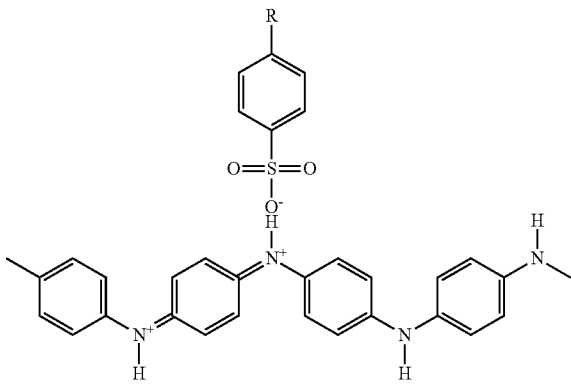

Pani: DBSA

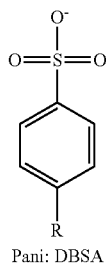

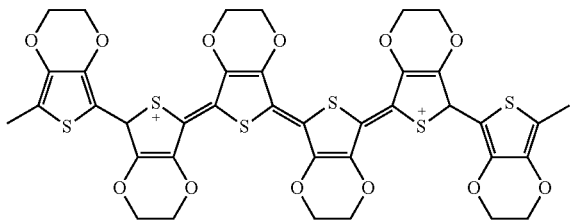

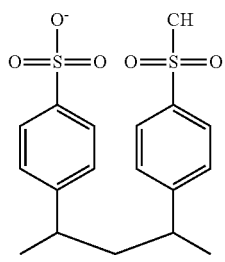

PEDOT: PSS

The R may be H or a C1-C10 alkyl group.

The self-doped conductive polymer may have a degree of polymerization of 13 to 10,000,000 and have a repeating unit represented by following Chemical Formula 21.

<Chemical formula 21>

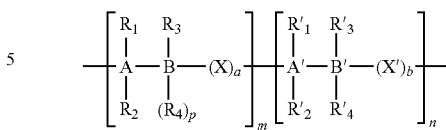

In Chemical Formula 21, $0<m<10,000,000$, $0<n<10,000,000$, and $0 \leq a \leq 20$, $0 \leq b \leq 20$ are satisfied;

at least one of $R_1$, $R_2$, $R_3$, $R'_1$, $R'_2$, $R'_3$, and $R'_4$ includes an ionic group, and each of A, B, A', and B' is independently selected from C, Si, Ge, Sn, or Pb;

each of $R_1$, $R_2$, $R_3$, $R'_1$, $R'_2$, $R'_3$, and $R'_4$ is independently selected from the group consisting of hydrogen, halogen, a nitro group, a substituted or unsubstituted amino group, a cyano group, a substituted or unsubstituted $C_1$-$C_{30}$ alkyl group, a substituted or unsubstituted $C_1$-$C_{30}$ alkoxy group, a substituted or unsubstituted $C_6$-$C_{30}$ aryl group, a substituted or unsubstituted $C_6$-$C_{30}$ arylalkyl group, a substituted or unsubstituted $C_6$-$C_{30}$ aryloxy group, a substituted or unsubstituted $C_2$-$C_{30}$ heteroaryl group, a substituted or unsubstituted $C_2$-$C_{30}$ heteroarylalkyl group, a substituted or unsubstituted $C_2$-$C_{30}$ heteroaryloxy group, a substituted or unsubstituted $C_5$-$C_{30}$ cycloalkyl group, a substituted or unsubstituted $C_5$-$C_{30}$ heterocycloalkyl group, a substituted or unsubstituted $C_1$-$C_{30}$ alkyl ester group, and a substituted or unsubstituted $C_6$-$C_{30}$ aryl ester group, and a hydrogen or halogen element is selectively bonded to carbon in Chemical Formula;

R4 is composed of a conjugated conductive polymer chain;

each of X and X' is independently selected from the group consisting of simple bond, O, S, a substituted or unsubstituted $C_1$-$C_{30}$ alkylene group, a substituted or unsubstituted $C_1$-$C_{30}$ heteroalkylene group, a substituted or unsubstituted $C_6$-$C_{30}$ arylene group, a substituted or unsubstituted $C_6$-$C_{30}$ arylalkylene group, a substituted or unsubstituted $C_2$-$C_{30}$ heteroarylene group, a substituted or unsubstituted $C_2$-$C_{30}$ heteroarylalkylene group, a substituted or unsubstituted $C_5$-$C_{20}$ cycloalkylene group, and a substituted or unsubstituted $C_5$-$C_{30}$ heterocycloalkylene aryl ester group, and a hydrogen or halogen element is selectively bonded to carbon in Chemical Formula.

For example, the ionic group includes an anionic group selected from the group consisting of $PO_3^{2-}$, $SO_3^-$, $COO^-$, $I^-$, and $CH_3COO^-$, a metal ion selected from $Na^+$, $K^+$, $Li^+$, $Mg^{+2}$, $Zn^{+2}$, and $Al^{+3}$, and a cationic group selected from the group consisting of $H^+$, $NH_4^+$, $CH_3(-CH_2-)_nO^+$ (where n is a natural number of 1 to 50) and mating with the anionic group.

For example, in the self-doped conductive polymer in Chemical Formula 100, at least one of $R_1$, $R_2$, $R_3$, $R'_1$, $R'_2$, $R'_3$, and $R'_4$ may be a fluorine or fluorine-substituted group, but is not limited thereto.

The conductive polymer, for example, a specific example of the conductive polymer is as follows, but is not limited thereto:

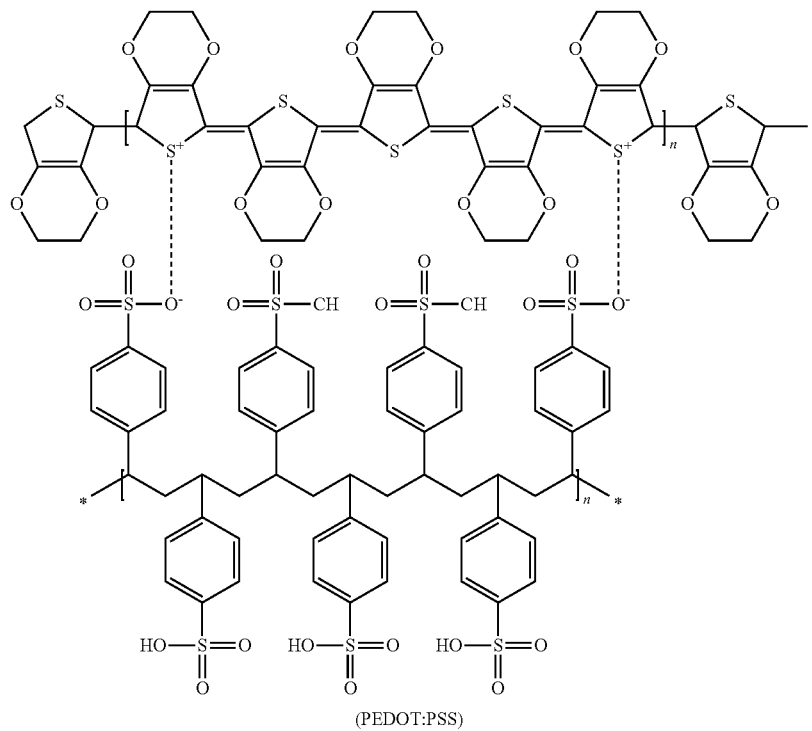
(PEDOT:PSS)
<Polymer 1>
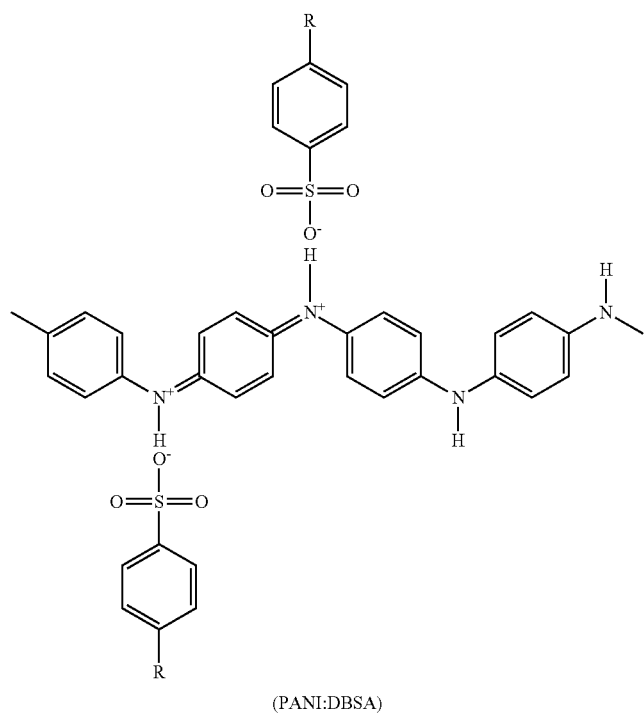
(PANI:DBSA)
<Polymer 2>

-continued
<Polymer 3>
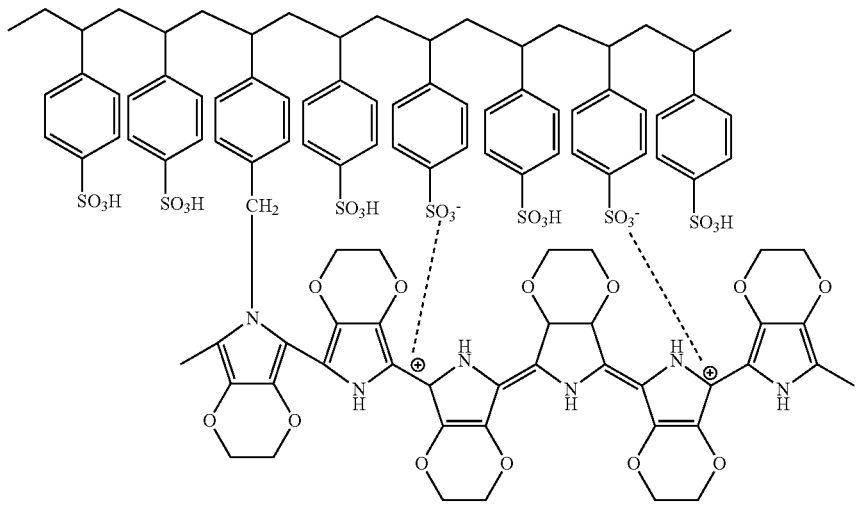
<Polymer 4>
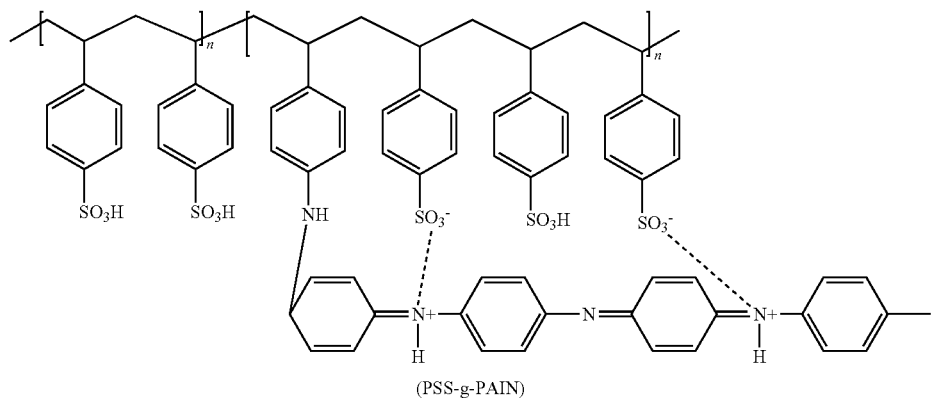
(PSS-g-PAIN)
<Polymer 5>
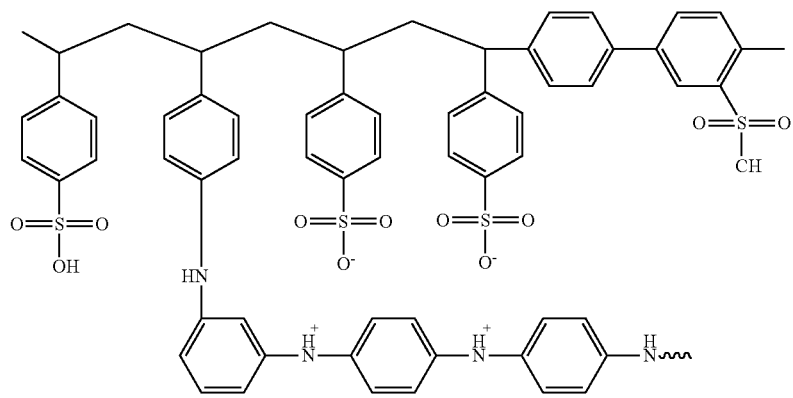

-continued
<Polymer 6>
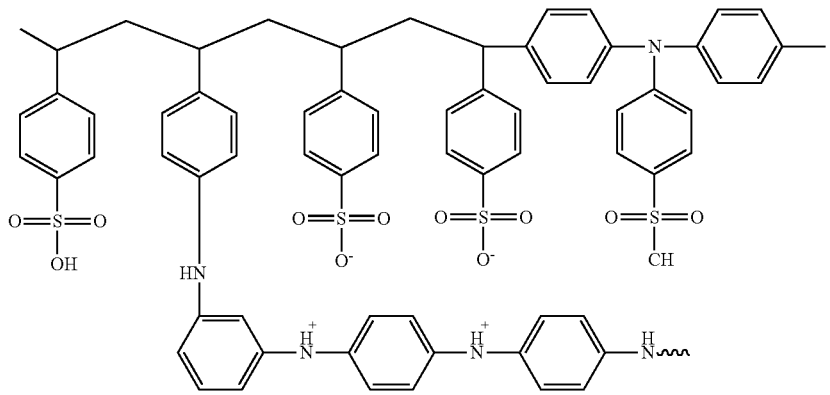
<Polymer 7>
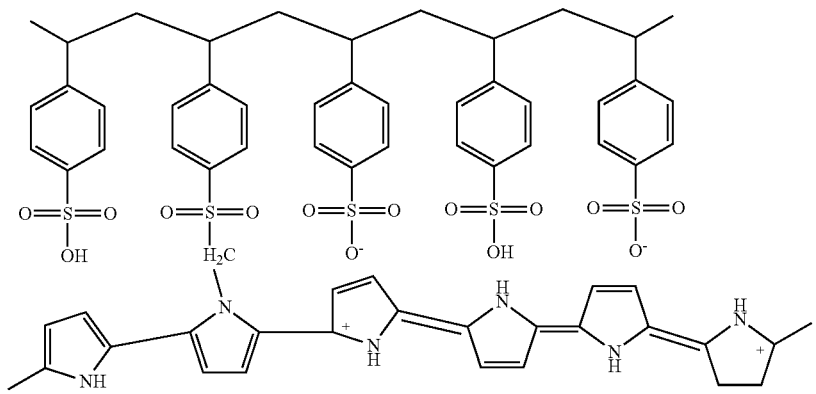
<Polymer 8>
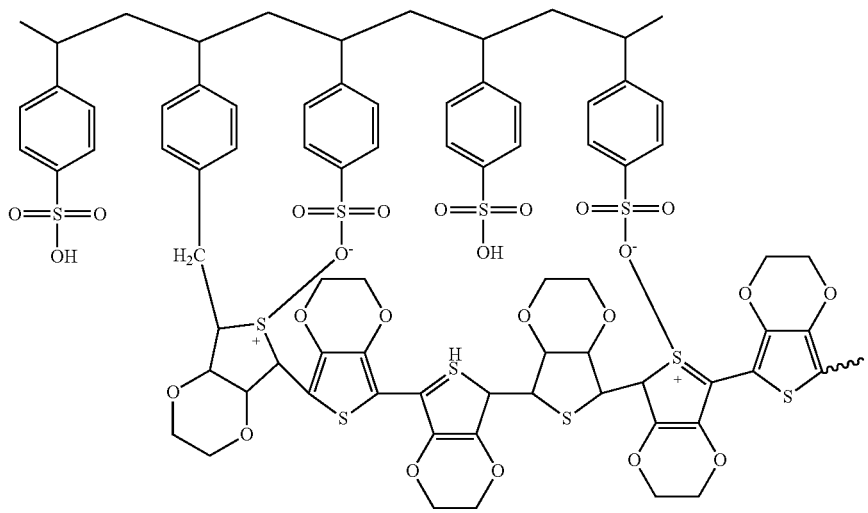
<Polymer 9>
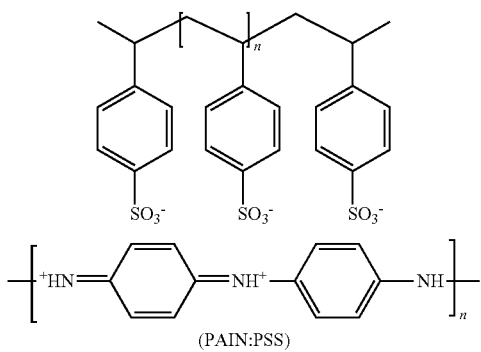
(PAIN:PSS)

-continued
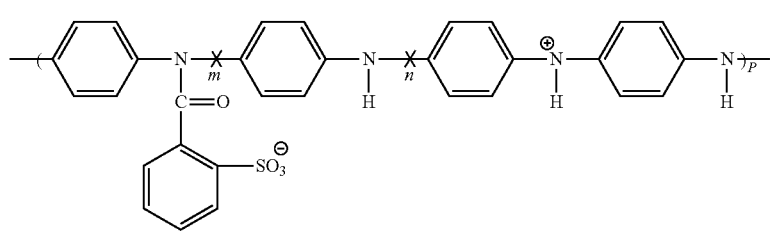
<Polymer 10>
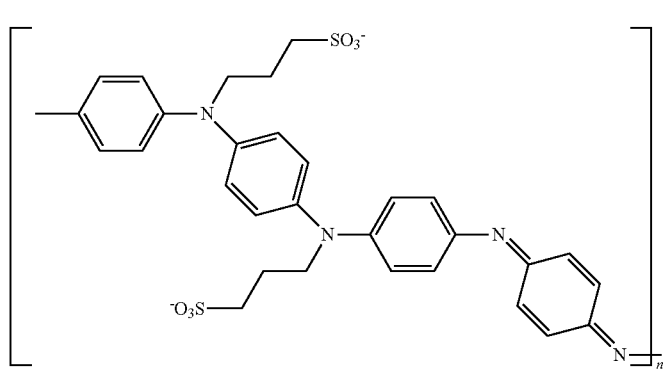
<Polymer 11>
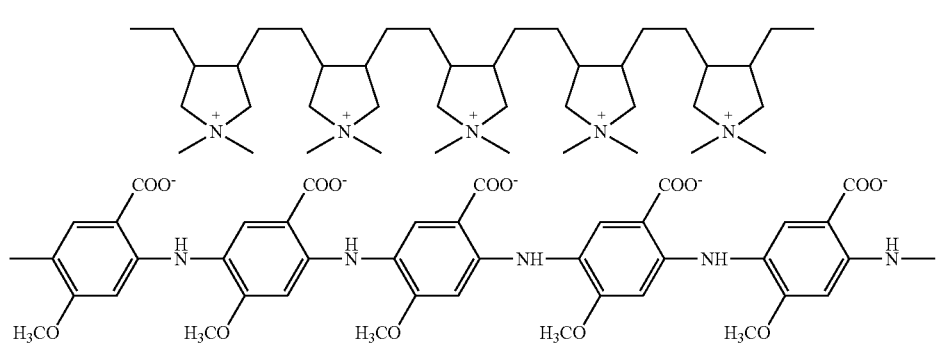
<Polymer 12>
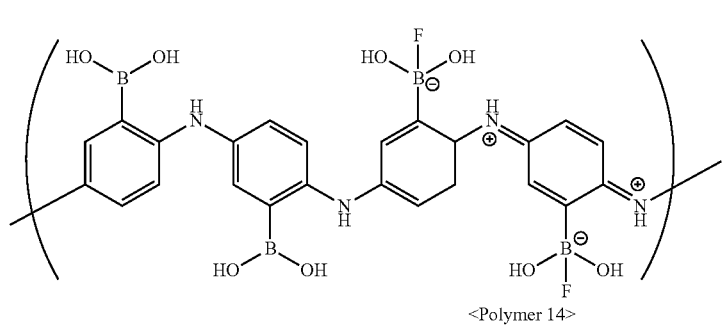
<Polymer 13>
<Polymer 14>
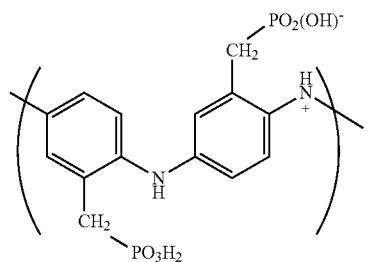
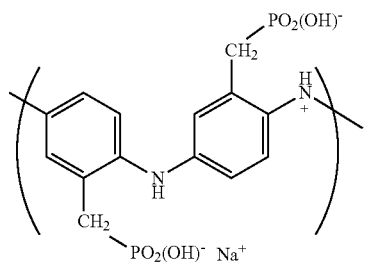
<Polymer 15>

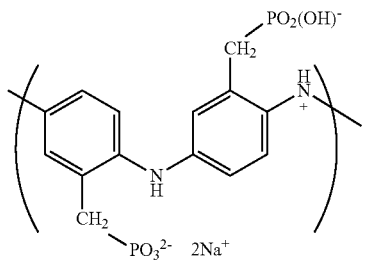
<Polymer 16>
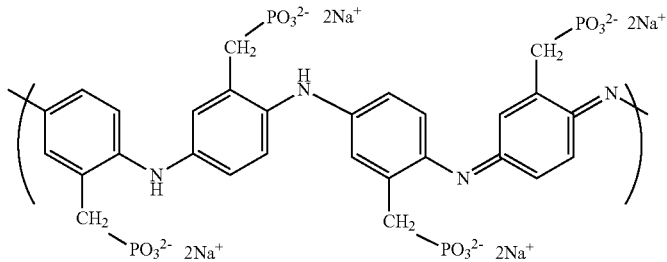
<Polymer 16>
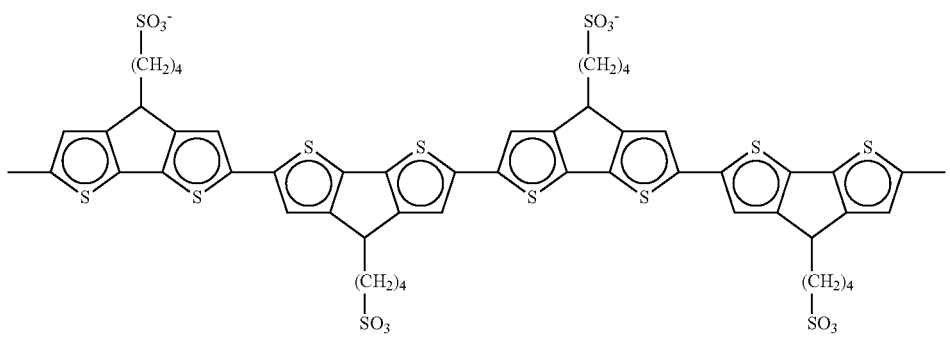
<Polymer 18>
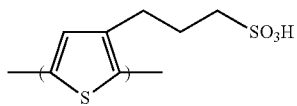
<Polymer 19>
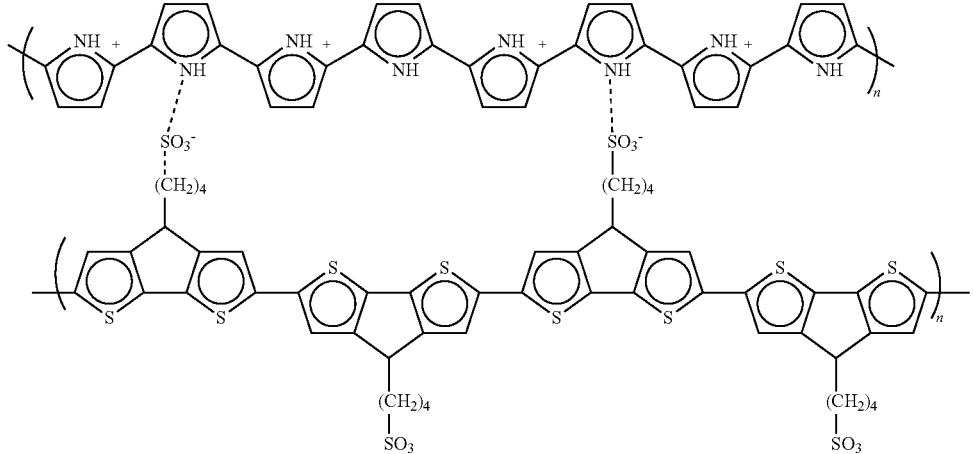
<Polymer 20>
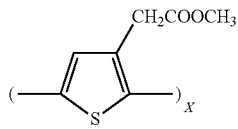
<Polymer 21>
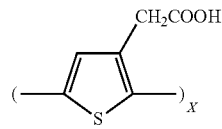
<Polymer 22>

<Polymer 23>

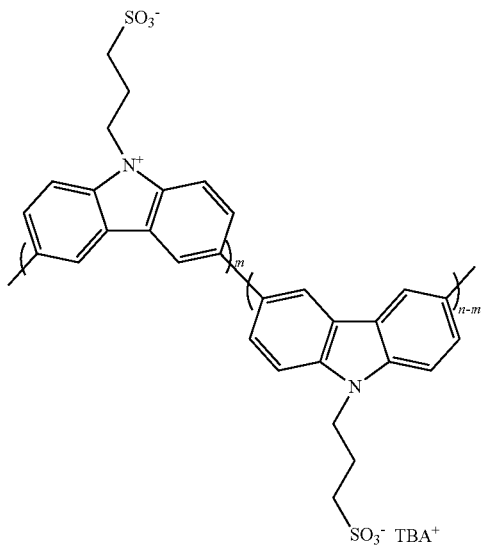

SO3⁻ TBA⁺

<Polymer 43>

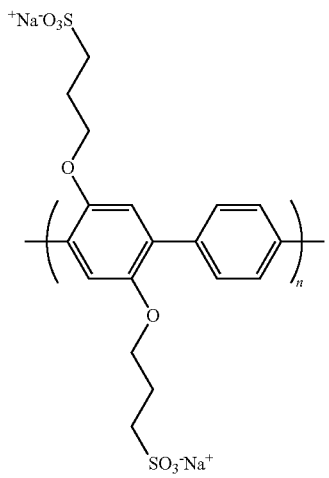

<Polymer 43>

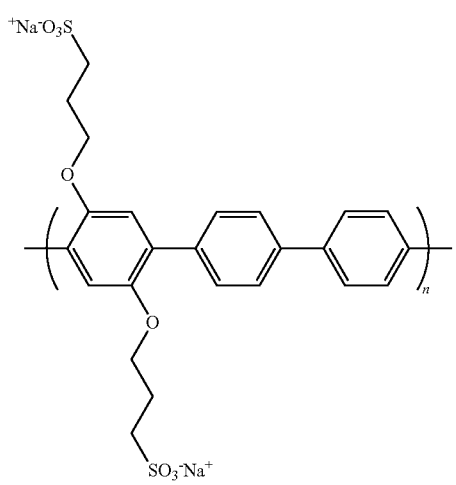

A specific example of the unsubstituted alkyl group in this specification may be methyl, ethyl, propyl, isobutyl, sec-butyl, tert-butyl, pentyl, iso-amyl, hexyl, and the like as a linear or branched type, and one or more hydrogen atoms included in the alkyl group may be substituted with a halogen atom, a hydroxy group, a nitro group, a cyano group, a substituted or unsubstituted amino group ((—NH2, —NH(R), —N(R')(R"), where each of R' and R" is an independent alkyl group having 1 to 10 carbon atoms), an amidino group, a hydrazine, or a hydrazone group, a carboxyl group, a sulfonic acid group, a phosphate group, a $C_1$-$C_{20}$ alkyl group, a $C_1$-$C_{20}$ halogenated alkyl group, a $C_1$-$C_{20}$ alkenyl group, a $C_1$-$C_{20}$ alkynyl group, a $C_1$-$C_{20}$ heteroalkyl group, a $C_6$-$C_{20}$ aryl group, a $C_6$-$C_{20}$ arylalkyl group, a $C_6$-$C_{20}$ heteroaryl group, or a $C_6$-$C_{20}$ heteroarylalkyl group.

The heteroalkyl group in this specification represents that at least one, preferably, 1 to 5 carbon atoms of the carbon atoms in the main chain of the alkyl group are substituted with hetero atoms such as an oxygen atom, a sulfur atom, a nitrogen atom, a phosphorus atom, and the like.

The aryl group in this specification represents a carbocycle aromatic system including one or more aromatic rings, and the rings may be attached together or fused by a pendant method. A specific example of the aryl group includes an aromatic group such as phenyl, naphthyl, tetrahydronaphthyl, and the like, and one or more hydrogen atoms of the aryl group may be substituted with the same substituent as the above-described alkyl group.

The heteroaryl group in this specification represents a ring aromatic system including 1, 2 or 3 heteroatoms selected from N, O, P, or S, and having 5 to 30 ring atoms with the remaining ring atoms C, and the rings may be attached together or fused by the pendant method. Also, one or more hydrogen atoms of the heteroaryl group may be substituted with the same substituent as the above-described alkyl group.

The alkoxy group in this specification represents radical-O-alkyl, wherein the alkyl is as defined above. A specific example of alkoxy group includes methoxy, ethoxy, propoxy, isobutyloxy, sec-butyloxy, pentyloxy, iso-amyloxy, hexyloxy, and the like, and at least one hydrogen atom of the alkoxy group may be substituted with the substituent, like the above-described alkyl group.

The heteroalkoxy group, which is a substituent used in the present invention, may be essentially same as the alkoxy except that at least one heteroatom such as oxygen, sulfur, or nitrogen are present in the alkyl chain, for example, may include $CH_3CH_2OCH_2CH_2O—$, $C_4H_9OCH_2CH_2OCH_2CH_2O—$, and $CH_3O(CH_2CH_2O)_nH$.

The arylalkyl group in this specification represents that a portion of hydrogen atoms in the aryl group is substituted with a radical such as lower alkyl, for example, methyl, ethyl, propyl, and the like. For example, the arylalkyl group may include benzyl, phenylethyl, and the like. Also, one or more hydrogen atoms of the arylalkyl group may be substituted with the same substituent as the above-described alkyl group.

The heteroarylalkyl group in this specification represents that a portion of the hydrogen atoms of the heteroaryl group is substituted with a lower alkyl group, and heteroaryl in the heteroarylalkyl group is as defined above. Also, one or more hydrogen atoms of the heteroarylalkyl group may be substituted with the same substituent as the above-described alkyl group.

The aryloxy group in this specification represents radical-O-aryl, wherein the aryl is as defined above. A specific example of the aryloxy group includes phenoxy, naphthoxy, anthracenyloxy, phenanthrenyloxy, fluorenyloxy, indenyloxy, and the like, and at least one hydrogen atom of the aryloxy group may be substituted with the substituent, like the above-described alkyl group.

The heteroaryloxy group in this specification represents radical-O-heteroaryl, wherein the heteroaryl is as defined above.

A specific example of the heteroaryloxy group in this specification includes benzyloxy, phenylethyloxy, and the like, and at least one hydrogen atom of the heteroaryloxy group may be substituted with the substituent, like the above-described alkyl group.

The cycloalkyl group in this specification represents a monovalent monocyclic system having 5 to 30 carbon atoms. Also, at least one of hydrogen atoms of the cycloalkyl group may be substituted with the same substituent as the above-described alkyl group.

The heterocycloalkyl group in this specification represents a monovalent monocyclic system including 1, 2 or 3 heteroatoms selected from N, O, P, or S, and having 5 to 30 ring atoms with the remaining ring atoms C. Also, one or more hydrogen atoms of the heterocycloalkyl group may be substituted with the same substituent as the above-described alkyl group.

The alkyl ester group in this specification represents a functional group having an alkyl group and an ester group bonded thereto, wherein the alkyl group is as defined above.

The heteroalkyl ester group in this specification represents a functional group having a heteroalkyl group and an ester group bonded thereto, wherein the heteroalkyl group is as defined above.

The aryl ester group in this specification represents a functional group having an aryl group and an ester group bonded thereto, wherein the aryl group is as defined above.

The heteroaryl ester group in this specification represents a functional group having a heteroaryl group and an ester group bonded thereto, wherein the heteroaryl group is as defined above.

The amino group used in the present invention represents $—NH_2$, $—NH(R)$ or $—N(R')(R'')$, and each of R' and R'' are an independent alkyl group having 1 to 10 carbon atoms.

Halogen in this specification is fluorine, chlorine, bromine, iodine, or astatine, more preferably, fluorine.

The metallic carbon nanotube is a purified metallic carbon nanotube itself or a carbon nanotube having metal particles (for example, Ag, Au, Cu, Pt particles, etc.), which are attached to an inner wall and/or an outer wall of the carbon nanotube.

The graphene is a graphene monolayer having a thickness of about 0.34 nm, a few layer graphene having a structure in which two to ten graphene monolayers are stacked, or a graphene multilayer structure having a structure in which a number of graphene monolayers greater than the number of the few layer graphenes are stacked.

The metal nanowire and the semiconductor nanowire may be selected from, for example, Ag, Au, Cu, Pt NiSix (nickel silicide) nanowires and two or more composites (for example, alloys or core-shell structures) nanowires of the above-described nanowires, but is not limited thereto.

The semiconductor nanowire may be selected from, for example, Si nanowires doped with Si, Ge, B or N, Ge nanowires doped with B or N, and two or more composites (for example, alloys or core-shell structures) of the above-described nanowires, but is not limited thereto.

Each of the nanowire and the semiconductor nanowire may have a diameter of 5 nm to 100 nm and a length of 500 nm to 100 μm. The diameter and length may be variously selected according to manufacturing methods of the metal nanowire and the semiconductor nanowire.

The metal grid is formed of metal wires crossing each other by using Ag, Au, Cu, Al, Pt, or an alloy thereof, and may have a line width of 100 nm to 100 μm, but a length of the metal grid is not limited. The metal grid may protrude from the first electrode or be recessed to be inserted into the first electrode.

The metal nano-dot may be selected from Ag, Au, Cu, Pt, and two or more composite (for example, alloys or core-shell structures) nano-dots, but is not limited thereto.

At least one moiety represented by $—S(Z_{100})$ and $—Si(Z_{101})(Z_{102})(Z_{103})$ may be bonded on the metal nanowire, the semiconductor nanowire, and the metal nano-dot surface (wherein the $Z_{100}$, $Z_{101}$, $Z_{102}$, and $Z_{103}$ independently include hydrogen, a halogen atom, a substituted or unsubstituted $C_1$-$C_{20}$ alkyl group or a substituted or unsubstituted $C_1$-$C_{20}$ alkoxy group). At least one moiety represented by $—S(Z100)$ and $—Si(Z_{101})(Z_{102})(Z_{103})$ is a self-assembled moiety. Here, since bonding force between the metal nanowires, the semiconductor nanowires, and the metal nano-dots or bonding force between the metal nanowires, the semiconductor nanowires, and the metal nano dots and the first electrode 210 is enhanced through the above-described moiety, electrical characteristics and the mechanical strength may be improved.

The above-described conductive oxide may be one of indium tin oxide (ITO), indium zinc oxide (IZO), $SnO_2$, and $InO_2$.

A method for forming the conductive layer 31 on the first electrode 20 may use a coating method, a cast method, a Langmuir-Blodgett (LB) method), an ink-jet printing method, a nozzle printing method, a slot-die coating method, a doctor blade coating method, a screen printing method, a dip coating method, a gravure printing method, a reverse-offset printing method, a physical transfer method, a spray coating method, a chemical vapor deposition method, or a thermal evaporation method.

Also, the conductive material may be mixed with a solvent to prepare a mixed solution, and then, be applied the first electrode 10 to remove the solvent through heat treatment. The above-mentioned solvent may include at least one selected from the group consisting of a polar solvent, for example, water, alcohol (e.g., methanol, ethanol, n-propanol, 2-propanol, n-butanol, and the like), formic acid, nitromethane, acetaic acid, ethylene glycol, glycerol, n-methyl-2-pyrrolidone (NMP), N-dimethylacetamide (N), dimethylformamide (DMF), dimethyl sulfoxide (DMSO), tetrahydrofuran (THF), ethyl acetate (EtOAc), acetone, and acetonitrile (MeCN).

When the conductive layer 31 includes the metal nano tube, the conductive layer may be formed by growing metallic carbon nano tube on the first electrode 20 or applying carbon nano tube, which is dispersed in the solvent, through the printing method (e.g., the spray coating method, the spin coating method, the dip coating method, the gravure coating method, the screen printing method, and the slot-die coating method).

When the conductive layer 31 includes the metallic grid, the conductive layer 31 may be formed by vacuum-depositing a metal on the first electrode 20 to form a metal layer, and then, by performing patterning into various mesh shapes through photolithography or dispersing metal precursor or the metal particles into the solvent to perform the printing method (the spray coating method, the spin coating method, the dip coating method, the gravure coating method, the screen printing method, and the slot-die coating method).

The conductive layer 31 may improve conductivity in the exciton buffer layer 30, and additionally, improve optical extraction by adjusting scattering, reflection, and absorption or give flexibility to improve mechanical strength.

The surface buffer layer 32 includes a fluorine-based material. The fluorine-based material is preferably a fluorine-based material having surface energy lower than that of the above-described conductive material and may have surface energy of 30 mN/m or less.

Also, the fluorine-based material may have hydrophobicity higher than that of the conductive polymer.

Here, in the surface buffer layer 32, the fluorine-based material may have a higher concentration on a second surface 32b opposite to a first surface 32a than that on the first surface 32a adjacent to the conductive layer 31.

The second surface 32b of the surface buffer layer 32 may have a work function of 5.0 eV or more. For example, a work function measured on the second surface 32b of the surface buffer layer 32 may be 5.0 eV to 6.5 eV, but is not limited thereto.

The fluorine-based material may be a perfluorinated ionomer or a fluorinated ionomer containing at least one F. Particularly, when the fluorine-based material is the fluorinated ionomer, the buffer layer may have a thick thickness, and phase-separation of the conductive layer 31 and the surface buffer layer 32 may be prevented to form a uniform exciton buffer layer 30.

The fluorine-based material may include at least one ionomer selected from the group consisting of ionomers having the following Chemical Formulas 1 to 12.

<Chemical Formula 1>

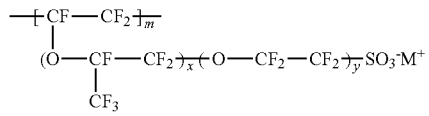

Where m is a number between 1 to 10,000,000, each of x and y is an independent number between 0 to 10, and $M^+$ is $Na^+$, $K^+$, $Li^+$, $H^+$, $CH_3(CH_2)_nNH_3^+$ (n is an integer between 0 to 50), $NH_4^+$, $NH_2^+$, $NHSO_2CF_3^+$, $CHO^+$, $C_2H_5OH^+$, $CH_3OH^+$, or $RCHO^+$ (R is $CH_3(CH_2)_n$; n is an integer between 0 to 50);

<Chemical Formula 2>

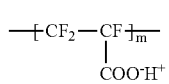

Where m is a number between 1 to 10,000,000;

<Chemical Formula 3>

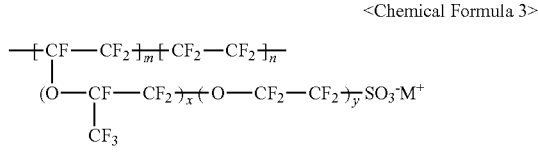

Where each of m and n is $0<m\leq10,000,000$, $0\leq n<10,000,000$, each of x and y is an independent number between 0 to 20, and $M^+$ is $Na^+$, $K^+$, $Li^+$, $H^+$, $CH_3(CH_2)_nNH_3^+$ (n is an integer between 0 to 50), $NH_4^+$, $NH_2^+$, $NHSO_2CF_3^+$, $CHO^+$, $C_2H_5OH^+$, $CH_3OH^+$, or $RCHO^+$ (R is $CH_3(CH_2)_n$—; n is an integer between 0 to 50);

<Chemical Formula 4>

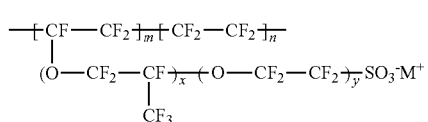

Where each of m and n is $0<m\leq10,000,000$, $0\leq n<10,000,000$, each of x and y is an independent number between 0 to 20, and $M^+$ is $Na^+$, $K^+$, $Li^+$, $H^+$, $CH_3(CH_2)_nNH_3^+$ (n is an integer between 0 to 50), $NH_4^+$, $NH_2^+$, $NHSO_2CF_3^+$, $CHO^+$, $C_2H_5OH^+$, $CH_3OH^+$, or $RCHO^+$ (R is $CH_3(CH_2)_n$—; n is an integer between 0 to 50);

<Chemical Formula 5>

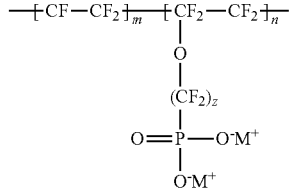

Where each of m and n is $0<m\leq10,000,000$, $0\leq n<10,000,000$, z is a number between 0 to 20, and $M^+$ is $Na^+$, $K^+$, $Li^+$, $H^+$, $CH_3(CH_2)_nNH_3^+$ (n is an integer between 0 to 50), $NH_4^+$, $NH_2^+$, $NHSO_2CF_3^+$, $CHO^+$, $C_2H_5OH^+$, $CH_3OH^+$, or $RCHO^+$ (R is $CH_3(CH_2)_n$—; n is an integer between 0 to 50);

<Chemical Formula 6>

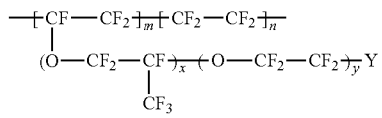

Where each of m and n is $0<m\leq10,000,000$, $0\leq n<10,000,000$, each of x and y is an independent number between 0 to 20, Y is one selected from —$COO^-M^+$, —$SO_3$—

$NHSO_2CF_3^+$, and $-PO_{32}\text{-}(M^+)_2$, and $M^+$ is $Na^+$, $K^+$, $Li^+$, $H^+$, $CH_3(CH_2)_nNH_3^+$ (n is an integer between 0 to 50), $NH_4^+$, $NH_2^+$, $NHSO_2CF_3^+$, $CHO^+$, $C_2H_5OH^+$, $CH_3OH^+$, or $RCHO^+$ (R is $CH_3(CH_2)_n-$; n is an integer between 0 to 50);

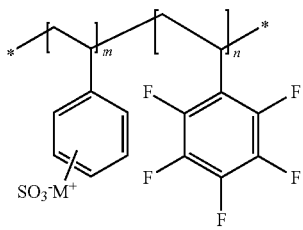

<Chemical Formula 7>

Where each of m and n is $0<m\leq10,000,000$, $0\leq n<10,000,000$, and $M^+$ is $Na^+$, $K^+$, $Li^+$, $H^+$, $CH_3(CH_2)_nNH_3^+$ (n is an integer between 0 to 50), $NH_4^+$, $NH_2^+$, $NHSO_2CF_3^+$, $CHO^+$, $C_2H_5OH^+$, $CH_3OH^+$, or $RCHO^+$ (R is $CH_3(CH_2)_n-$; n is an integer between 0 to 50);

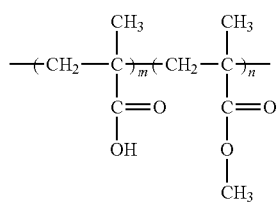

<Chemical Formula 8>

Where, each of m and n is a number satisfying a condition: $0<m\leq10,000,000$, $0\leq n<10,000,000$.

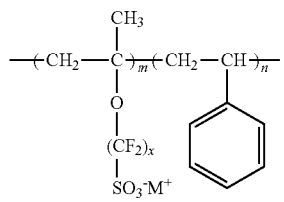

<Chemical Formula 9>

Where each of m and n is $0<m\leq10,000,000$, $0\leq n<10,000,000$, x is a number between 0 to 20, and $M^+$ is $Na^+$, $H^+$, $CH_3(CH_2)_nNH_3^+$ (n is an integer between 0 to 50), $NH_4^+$, $NH_2^+$, $NHSO_2CF_3^+$, $CHO^+$, $C_2H_5OH^+$, $CH_3OH^+$, or $RCHO^+$ (R is $CH_3(CH_2)_n-$; n is an integer between 0 to 50);

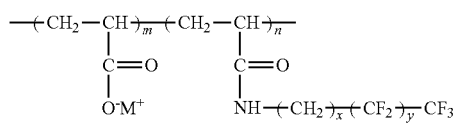

<Chemical Formula 10>

Where each of m and n is $0<m\leq10,000,000$, $0\leq n<10,000,000$, each of x and y is an independent number between 0 to 20, and $M^+$ is $Na^+$, $K^+$, $Li^+$, $H^+$, $CH_3(CH_2)_mNH_3^+$ (n is an integer between 0 to 50), $NH_4^+$, $NH_2^+$, $NHSO_2CF_3^+$, $CHO^+$, $C_2H_5OH^+$, $CH_3OH^+$, or $RCHO^+$ (R is $CH_3(CH_2)_n-$; n is an integer between 0 to 50);

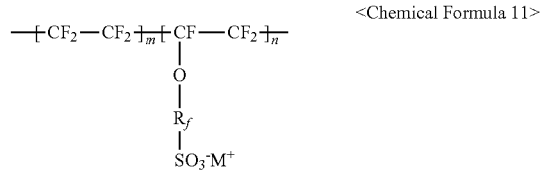

<Chemical Formula 11>

Where each of m and n is $0<m\leq10,000,000$, $0\leq n<10,000,000$, Rf is $-(CF_2)_z-$ (z is an integer between 1 to 50, and 2 is excluded), $-(CF_2CF_2O)_zCF_2CF_2-$ (z is an integer between 1 to 50), or $-(CF_2CF_2CF_2O)_zCF_2CF_2-$ (z is an integer between 1 to 50), and $M^+$ is $Na^+$, $K^+$, $Li^+$, $H^+$, $CH_3(CH_2)_nNH_3^+$ (n is an integer between 0 to 50), $NH_4^+$, $NH_2^+$, $NHSO_2CF_3^+$, $CHO^+$, $C_2H_5OH^+$, $CH_3OH^+$, or $RCHO^+$ (R is $CH_3(CH_2)_n-$; n is an integer between 0 to 50);

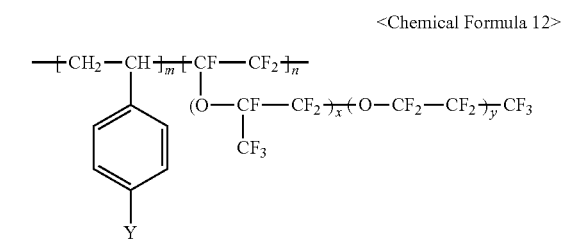

<Chemical Formula 12>

Where each of m and n is $0<m\leq10,000,000$, $0\leq n<10,000,000$, each of x and y is an independent number between 0 to 20, Y is independent one selected from $-COO\text{-}M^+$, $-SO_3-NHSO_2CF_3^+$, and $-PO_{32}\text{-}(M^+)_2$, and $M^+$ is $Na^+$, $K^+$, $Li^+$, $H^+$, $CH_3(CH_2)_nNH_3^+$ (n is an integer between 0 to 50), $NH_4^+$, $NH_2^+$, $NHSO_2CF_3^+$, $CHO^+$, $C_2H_5OH^+$, $CH_3OH^+$, or $RCHO^+$ (R is $CH_3(CH_2)_n-$; n is an integer between 0 to 50);

Also, the fluorine-based material may include at least one ionomer or fluorinated low molecular selected from the group consisting of ionomers or fluorinated low meculars having a structure of the following Chemical Formulas 13 to 19.

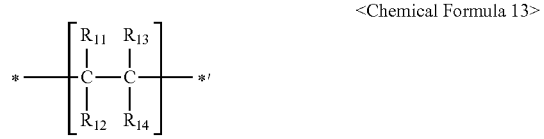

<Chemical Formula 13>

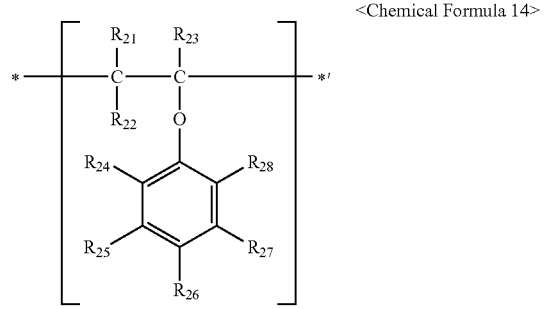

<Chemical Formula 14>

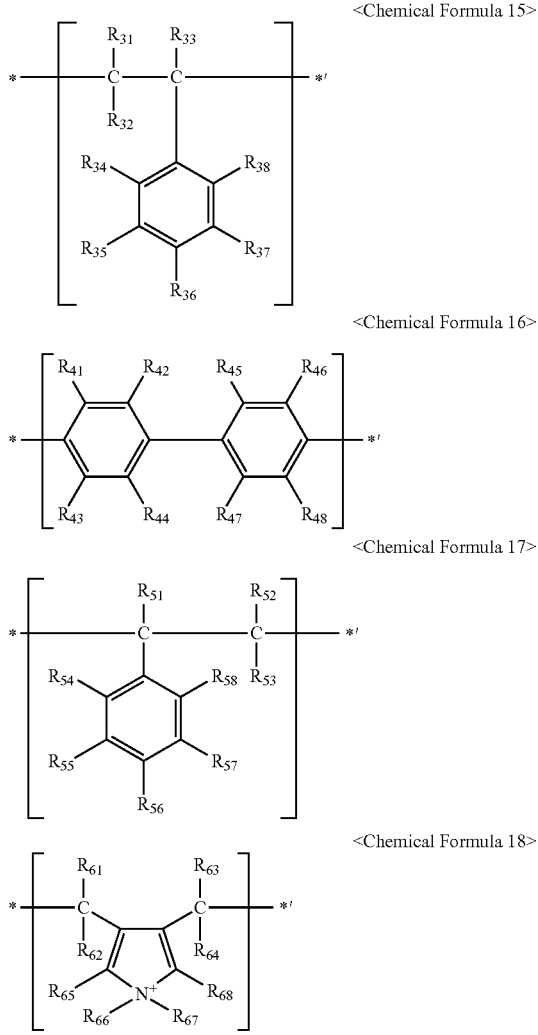

<Chemical Formula 15>
<Chemical Formula 16>
<Chemical Formula 17>
<Chemical Formula 18>

(In Chemical Formulas 13 to 18, $R_{11}$ to $R_{14}$, $R_{21}$ to $R_{28}$, $R_{31}$ to $R_{38}$, $R_{41}$ to $R_{48}$, $R_{51}$ to $R_{58}$, and $R_{61}$ to $R_{68}$ are independently selected from —F, a $C_1$-$C_{20}$ alkyl group, a $C_1$-$C_{20}$ alkoxy group, $C_1$-$C_{20}$ alkyl group substituted with at least —F, C1-$C_{20}$ alkoxy group substituted with at least —F, $Q_1$, —O—$(CF_2CF(CF_3)$—$O)_n$—$(CF_2)$m-$Q_2$ (where, n and m are independent from each other, each is an integer between 0 to 20, and n+m is a number equal to or greater than 1), and —$(OCF_2CF_2)$x-$Q_3$ (where, x is an integer of 1 to 20, the each of $Q_1$ to $Q_3$ is an ionic group, and the ionic group includes an anionic group and a cationic group, the anionic group is selected from $PO_{32}$—, $SO_3$—, COO—, I—, $CH_3COO$—, and $BO_{22}$—, the cationic group includes at least one of a metal ion and an organic ion, the metal ion is selected from $Na^+$, $K^+$, $Li^+$, $Mg^{+2}$, $Zn^{+2}$ and $Al^{+3}$, and the organic ion is selected from $H^+$, $CH_3(CH_2)_{n1}NH_3^+$ (where, n is an integer between 0 to 50), $NH_4^+$, $NH_2^+$, $NHSO_2CF_3^+$, $CHO^+$, $C_2H_5OH^+$, $CH_3OH^+$, and $RCHO^+$ (where, R is $CH_3(CH_2)_{n2}$—, and n2 is an integer between 0 to 50);

At least one of R11 to R14, at least one of R21 to R28, at least one of R31 to R38, at least one of R41 to R48, at least one of $R_{51}$ to $R_{58}$, and at least one of R61 to R68 is selected from —F, C1-$C_{20}$ alkyl group substituted with at least —F, C1-$C_{20}$ alkoxy group substituted with at least —F, —O—$(CF_2CF(CF_3)$—$O)_n$—$(CF2)$m-$Q_2$, and —$(OCF2CF2)$x-$Q_3$.)

$X$-$M^f_n$-$M^h_m$-$M^a_r$-$G$ <Chemical Formula 19>

(In Chemical Formula 19,

X is a terminal group;

Mf represents a unit derived from a fluorinated monomer obtained from condensation reaction of perfluoropolyether alcohol, polyisocyanate, and an isocyanate reactive-nonfluorinated monomer;

Mh represents a unit derived from a non-fluorinated monomer;

Ma represents a unit having a silyl group represented by —$Si(Y_4)(Y_5)(Y_6)$;

$Y_4$, $Y_5$, and $Y_6$ independently represent a substituted or unsubstituted $C_1$-$C_{20}$ alkyl group, a substituted or unsubstituted $C_6$-$C_{30}$ aryl group, or a hydrolyzable substituent, and at least one of $Y_4$, $Y_5$, and $Y_6$ represents the above described hydrolyzable substituent.

G is a monovalent organic group containing a residue of a chain transfer agent;

n is a number of 1 to 100;

m is a number of 0 to 100;

r is a number of 0 to 100;

n+m+r is at least 5.

The surface buffer layer 32 may have a thickness of 20 nm to 500 nm, for example, 50 nm to 200 nm. When the thickness of the surface buffer layer 32 satisfies the above-described range, excellent work function characteristics, transmittance, and flexible characteristics may be provided.

The surface buffer layer 32 may be formed through thermal treatment after a mixed solution containing the above-described fluorine-based material and a solvent is applied on the conductive layer 31.

The formed exciton buffer layer 30 may have a thickness of about 50 nm to about 1000 nm. Since the conductive layer 31 is formed, the conductivity may be improved, and also, since the surface buffer layer 32 is formed, the surface energy may be reduced. Therefore, the luminescent characteristics may be maximized.

The surface buffer layer 32 may further include at least one additive selected from the group consisting of carbon nanotubes, graphenes, reduced oxide graphenes, metal nanowires, metal carbon nanotubes, semiconductor quantum dots, semiconductor nanowires, and metal nano dots. When the additive is further added, the conductivity of the exciton buffer layer 30 may be maximized.

Also, the surface buffer layer 32 may further include a crosslinking agent including a bis(phenyl azide) material. When the surface buffer layer further includes the crosslinking agent, composition separation due to a time and device driving may be prevented. Thus, resistance and the work function of the exciton buffer layer 30 may be reduced to improve stability and reproducibility of the light emitting device.

The bis(phenyl azide) material may be a bis(phenyl azide) material of the following Chemical Formula 20.

<Chemical Formula 20>

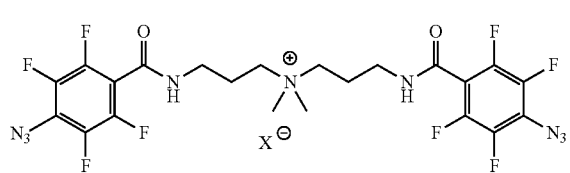

A method for forming the surface buffer layer 32 on the conductive layer 31 may use a coating method, a cast method, a Langmuir-Blodgett (LB) method), an ink-jet printing method, a nozzle printing method, a slot-die coating method, a doctor blade coating method, a screen printing method, a dip coating method, a gravure printing method, a reverse-offset printing method, a physical transfer method, a spray coating method, a chemical vapor deposition method, or a thermal evaporation method.

However, although the conductive layer 31 and the surface buffer layer 32 are successively deposited in the step of forming the exciton buffer layer 30 as described above, the conductive material and the fluorine-based material may be mixed with each other, and then, the mixture may be applied on the first electrode and thermally treated to form the exciton buffer layer 30.

In this case, since the mixed solution is thermally treated, the conductive layer 31 and the surface buffer layer 32 may be successively self-assembled on the first electrode 20. Therefore, the manufacturing process may be maximized.

The fluorine-based material may be a material having solubility of 90% or more, for example, solubility of 95% or more with respect to the polar solvent. Examples of the polar solvents include water, alcohols (methanol, ethanol, n-propanol, 2-propanol, n-butanol, etc.), ethylene glycol, glycerol, dimethylformamide (DMF), dimethylsulfoxide (DMSO), but is not limited thereto.

Figure 13:
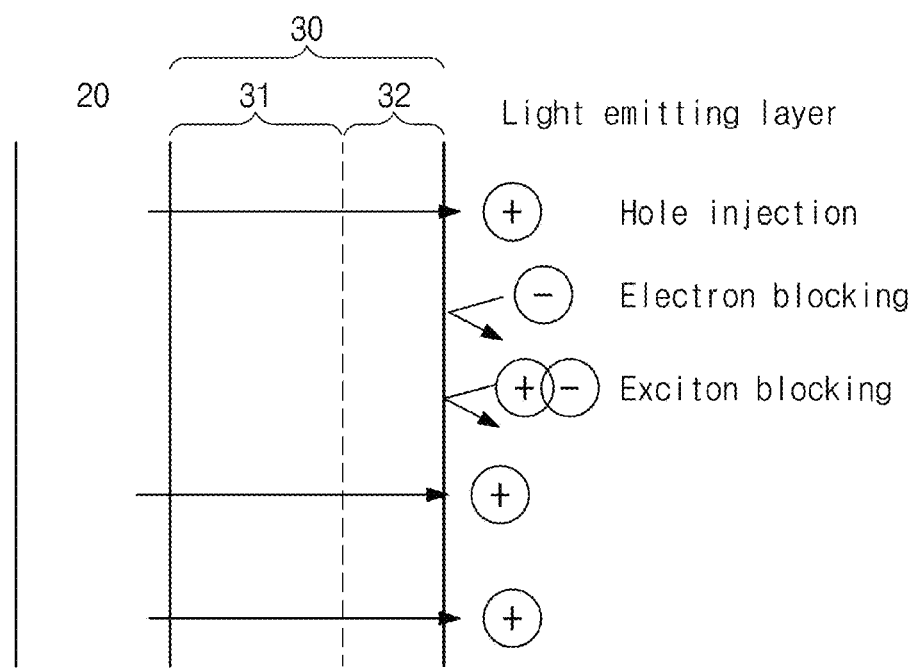
FIG. 13 is a schematic view illustrating an effect of an exciton buffer layer 30 according to an embodiment of the present invention.

FIG. 13 is a schematic view illustrating an effect of an exciton buffer layer 30 according to an embodiment of the present invention.

Referring to FIG. 13, the exciton buffer layer 30 according to an embodiment of the present invention may improve hole injection efficiency and serve as electron blocking to suppress quenching of the exciton.

The exciton buffer layer 30 may further include a crosslinking agent.

The crosslinking agent may be added to the exciton buffer layer 30 to prevent composition separation from occurring due to a time and device driving. When the surface buffer layer 32 is formed, deterioration in efficiency of the exciton buffer layer 30 due to the use of the solution may be prevented. Therefore, the stability and the reproductively of the device may be improved.

The crosslinking agent may include at least one functional group selected from the group consisting of an amine group ($-NH_2$), a thiol group (—SH), and a carboxyl group.

The crosslinking agent may include at least one selected from the group consisting of a bis(phenyl azide)-based material, a diaminoalkane-based material, a dithiol-based material, dicarboxylate, an ethylene glycol di(meth)acrylate derivative, a methylenebisacrylamide derivative, and DVB.

A hole transport layer may be formed on the exciton buffer layer 30. The hole transport layer may be formed according to a method arbitrarily selected from various known methods such as a vacuum evaporation method, a spin-coating method, a cast method, an LB method, and the like. Here, if the vacuum deposition method is selected, although are different according to a target compound, a layer structure, a thermal property, and the like, deposition conditions may be selected within a deposition temperature range of 100° C. to 500° C., a vacuum degree range of $10^{-10}$ torr to $10^{-3}$ torr, and a deposition rate range of 0.01 Å/sec to 100 Å/sec. if the spin-coating method is selected, although are different according to a target compound, a layer structure, a thermal property, and the like, coating conditions may be selected within a coating rate range of 2000 rpm to 5000 rpm and a thermal treating temperature (a thermal treating temperature for removing the solvent after the coating) of 80° C. to 200° C.

The hole transport layer material may be selected from materials capable of transporting holes better than hole injection. The hole transport layer may be formed using a known hole transporting material, for example, an amine-based material having an aromatic condensed ring and a triphenylamine-based material.

More particularly, examples of the hole transporting material may include 1,3-bis(carbazol-9-yl)benzene (MCP), 1,3,5-tris(carbazol-9-yl)benzene (TCP), 4,4',4"-tris(carbazol-9-yl)triphenylamine (TCTA), 4,4'-bis(carbazol-9-yl)biphenyl (CBP), N,N'-bis(naphthale$_{n-1}$-yl)-N,N'-bis(phenyl)-benzidine (NPB), N,N'-bis(naphthalen-2-yl)-N,N'-bis(phenyl)-benzidine (β-NPB), N,N'-bis(naphthale$_{n-1}$-yl)-N,N'-bis(phenyl)-2,2'-dimethylbenzidine (α-NPD), di-[4-(N,N-ditolyl-amino)-phenyl]cyclohexane (TAPC), N,N,N',N'-tetra-naphthalen-2-yl-benzidine (β-TNB), N4,N4,N4',N4'-tetra(biphenyl-4-yl)biphenyl-4,4'-diamine (TPD15), poly(9,9-dioctylfluorene-co-bis-N,N'-(4-butylphenyl)-bis-N,N'-phenyl-1,4-phenylenediamine) (PFB), poly(9,9'-dioctylfluorene-co-N-(4-butylphenyl)diphenylamine) (TFB), poly(9,9'-dioctylfluorene-co-bis-N,N'-(4-butylphenyl)-bis-N,N'-phenylbenzidine) (BFB), poly(9,9-dioctylfluorene-co-bis-N,N'-(4-methoxyphenyl)-bis-N,N'-phenyl-1,4-phenylenediamine) (PFMO), but is not limited thereto.

The hole transport layer may have a thickness of 5 nm to 100 nm, for example, 10 nm to 60 nm. When the hole transport layer has a thickness within the above-described range, satisfactory hole transport characteristics may be achieved without increasing in driving voltage. However, the hole transport layer may be omitted.

Thus, the light emitting device including the exciton buffer layer 30 may have excellent efficiency, luminance, and lifetime characteristics without forming the hole injection layer. Thus, costs for manufacturing the light emitting device may be reduced.

When it is assumed that the hole transport layer is formed, the work function of the hole transport layer may be Z eV, where Z may be a real number between 5.2 to 5.6, but is not limited thereto.

$Y_1$ that is a work functional value of a first surface 32a of the surface buffer layer 32 of the exciton buffer layer 30 may range from 4.6 to 5.2, for example, 4.7 to 4.9. Also, $Y_1$ that is a work functional value of a second surface 32b of the surface buffer layer 32 of the exciton buffer layer 30 may be equal to or less than that of the fluorine-based material contained in the surface buffer layer 32. For example, the Y2 may be 5.0 to 6.5, e.g., 5.3 to 6.2, but is not limited thereto.

Figure 12C:
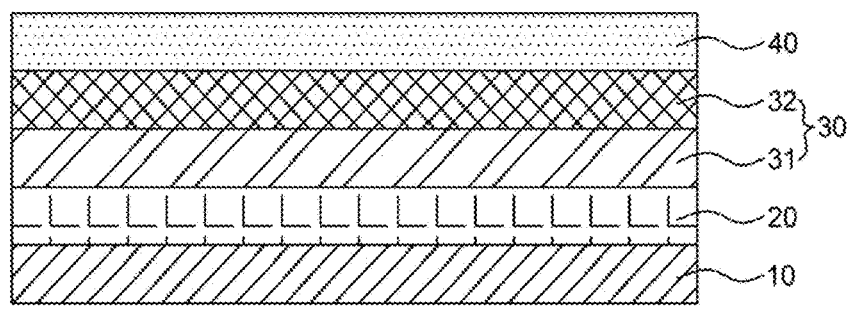

Referring to FIG. 12c, a solution including an organic-inorganic-hybrid perovskite nanoparticle including an organic-inorganic-hybrid perovskite nanocrystal structure is applied on the exciton buffer layer 30 to form a light emitting layer 40 including a first thin film of a nanoparticle.

The contents relating to the formation of the light emitting layer have the same constitution and function as those of the '<light layer for organic-inorganic-hybrid perovskite light emitting device>', reference will be made to the foregoing description.

Figure 12D:
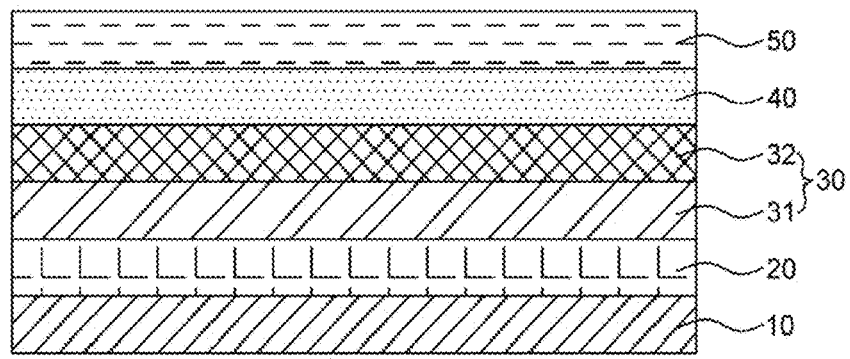

Thereafter, referring to FIG. 12d, a second electrode 50 is formed on the light emitting layer 40.

The second electrode 50 is an electrode into which an electron is injected and made of a conductive material. The second electrode 50 may be a metal, particularly, Al, Au, Ag, Cu, Pt, W, Ni, Zn, Ti, Zr, Hf, Cd, or Pd.

A process of depositing the second electrode 50 may include physical vapor deposition (PVD), chemical vapor deposition (CVD), sputtering, pulsed laser deposition (PLD), thermal evaporation, electron beam evaporation, atomic layer deposition (ALD), and molecular beam epitaxy (MBE).

The light emitting device includes a first electrode 20, an exciton buffer layer 30 which is disposed on the first electrode 20 and in which a conductive layer 31 including a conductive material and a surface buffer layer 32 including a fluorine-based material are successively stacked, a light emitting layer 40 disposed on the exciton buffer layer 30 and including an organic-inorganic-hybrid perovskite nanoparticle light-emitter, and a second electrode 50 disposed on the light emitting layer 40.

Here, since the exciton buffer layer 30 is formed, the light emitting device having the low work function and the high conductivity may be manufactured. In the light emitting layer including the first thin film of the nanoparticle, which includes the nanoparticle including the organic-inorganic-hybrid perovskite nanocrystal structure, organic-inorganic-hybrid perovskite having a crystal structure, in which an FCC and a BCC are combined with each other, may be formed in the nanoparticle, an a lamellar structure, in which an organic plane and an inorganic plate are alternately stacked, may be formed, and excitons may be confined in the inorganic plane to implement high color purity.

The light emitting device may be a laser diode or an LED.

For another example, the organic-inorganic-hybrid perovskite nanocrystal particle and the inorganic metal halide perovskite nanocrystal particle may be applied to a solar cell by using a photoactive layer including the above-described organic-inorganic-hybrid perovskite nanocrystal particle and the inorganic metal halide perovskite nanocrystal particle. The solar cell may include a first electrode, a second electrode, and a photoactive layer disposed between the first electrode and the second electrode and including the above-described perovskite nanocrystal particle.

Hereinafter, experimental examples will be described in order to facilitate understanding of the present invention. It should be understood, however, that the following examples are for the purpose of promoting understanding of the present invention and are not intended to limit the scope of the present invention.

Manufacturing Example 1—Manufacture of Solution Including Organic-Inorganic-Hybrid Perovskite Colloidal Nanoparticle A solution including an organic-inorganic-hybrid perovskite colloidal nanoparticle including an organic-inorganic-hybrid perovskite nanocrystal structure according to an embodiment of the present invention was formed. The colloidal solution was formed through an inverse nano-emulsion method, or reprecipitation method, or hot injection method.

Particularly, organic-inorganic-hybrid perovskite was dissolved in a polar solvent to prepare a first solution. Here, dimethylformamide was used as the polar solvent, and $(CH_3NH_3)_2PbBr_4$ was used as the organic-inorganic-hybrid perovskite. Here, the used $(CH_3NH_3)_2PbBr_4$ was prepared by mixing $CH_3NH_3Br$ with $PbBr_2$ at a ratio of 2:1.

Also, a second solution in which an alkyl halide surfactant is dissolved in a non-polar solvent was prepared. Here, toluene was used as the non-polar solvent, and octadecylammonium bromide $(CH_3(CH_2)_{17}NH_3Br)$ was used as the alkyl halide surfactant.

Then, the first solution slowly dropped drop wise into the second solution that is being strongly stirred to form the solution including the organic-inorganic-hybrid perovskite nanoparticle including the organic-inorganic-hybrid perovskite nanocrystal structure.

Manufacturing Example 2—Manufacture of Light Emitting Layer

First, a 10 wt % 3-mercaptopropionic acid (MPA, Aldrich) ethanolic solution was spin-coated on a glass substrate to form an anchoring agent layer. After the excess MPA is removed through washing using ethanol and chloroform, the perovskite nanocrystal manufactured by Manufacturing Example 1 was spin-coated on the anchoring agent layer to form a perovskite nanocrystal layer (2500 rpm and 20 s).

The perovskite nanocrystal that is not anchored through the chloroform spin-costing (2500 rpm and 20 s) was removed. To adjust a thickness of the perovskite nanocrystal layer, spin-coating (2500 rpm and 20 s) of a 1 wt % 1,2-ethanedithiol (EDT)/ethanol solution having 250 μL and spin-coating (2500 rpm and 20 s) of the perovskite nanocrystal solution was spin-coated (2500 rpm and 20 s) were repeatedly performed to form the light emitting device.

Manufacturing Example 3—Manufacture of Light Emitting Layer

First, a trioctylphosphine oxide (TOPO) solution and a trioctylphosphine (TOP) solution was added to the perovskite nanocrystal solution manufactured by Embodiment 1 to substitute a ligand of the perovskite nanocrystal with TOPO and TOP. Then, N,N'-diphenyl,N'-bis(3-methylphenyl)-(1,1'-biphenyl)-4,4'-diamine(TPD) was mixed with perovskite nanocrystal solution at a ratio of 100:5 (w/w) to manufacture a TPD-perovskite nanocrystal solution. The TPD-perovskite nanocrystal solution was spin-coated (500 rpm 7 s, 3000 rpm, and 90 s) to form a TPD and perovskite nanocrystal layer. Here, the TPD and perovskite nanocrystal was phase-separated while the spin-coating to form a nano thin film including the organic-inorganic-hybrid perovskite nanoparticle including the perovskite nanocrystal structure on the TPD layer.

Manufacturing Example 4—Manufacture of Light Emitting Layer

First, a Si native wafer was dipped into a octadecyltrichlorosilane (ODTS) solution to manufacture an ODTS-treated wafer. Also, a perovskite nanocrystal was spin-coated (1500 rpm and 60 s) on the ODTS-treated wafer to form a perovskite nanocrystal layer. Polydimethylsiloxane (PDMS) was poured on a flat silicon wafer and cured at a temperature of 75° C. for 2 hours to manufacture a PDMS stamp. The PDMS stamp was completely closely attached to the perovskite nanocrystal layer to apply a sufficient pressure, and then rapidly remove the stamp, thereby separating the perovskite nanocrystal from the ODTS-treated wafer. The separated perovskite nanocrystal was separated from the PDMS through contact with a previously prepared indium tin oxide (ITO)/PEDOT:PSS substrate.

Manufacturing Example 5—Manufacture of Light Emitting Layer

Tris(4-carbazoyl-9-ylphenyl)amine (TCTA), 1,3,5-tris(N-phenylbenzimidazole-2-yl)benzene (TPBi) was mixed with the perovskite nanocrystal solution at a ratio of 10:10:1 (w/w) to manufacture a TCTA-TPBi-perovskite nanocrystal solution. The TCTA-TPBi-perovskite nanocrystal solution was spin-coated (500 rpm 7 s, 3000 rpm, and 90 s) to form a TCTA-TPBi-perovskite nanocrystal layer.

Manufacturing Example 6—Manufacture of Light Emitting Device

A light emitting device according to an embodiment of the present invention was manufactured.

First, after an ITO substrate (a glass substrate coated with an ITO anode) is prepared, a mixed solution of PEDOT:PSS (CLEVIOS PH of Heraeus company) that is a conductive material and a material of a polymer 26 that is a fluorine-based material was spin-coated on the ITO anode and then thermally treated for 30 minutes at a temperature of 150° C. to form an exciton buffer layer having a thickness of 40 nm.

After the thermal treatment, the conductive layer in which 50% or more of a conductive polymer is contained and the surface buffer layer in which 50% or more of the polymer 1 material was successively stacked on the ITO anode to from a multi-layered exciton buffer layer. That is, the conductive layer and the surface buffer layer may be formed through the self-assembly.

A weight ratio of the exciton buffer layer including the conductive layer and the surface buffer layer is 1:6:25.4 for PEDOT:PSS:polymer 1, and the work function is 5.95 eV.

A $CH_3NH_3PbBr_3$ perovskite light emitting layer was formed on the exciton buffer layer using the method for manufacturing the light emitting layer according to Embodiment 2.

Thereafter, 1,3,5-Tris(1-phenyl-1H-benzimidazol-2-yl) benzene (TPBI) having a thickness of 50 nm was deposited on the light emitting layer under a high vacuum state of $1\times10^{-7}$ Torr or more to form an electron transport layer, and then, LiF having a thickness of 1 nm was deposited on the electron transport layer to form an electron injection layer. Then, aluminum having a thickness of 100 nm was deposited on the electron injection layer to form a cathode, thereby manufacturing an organic-inorganic-hybrid perovskite light emitting device. The manufactured light emitting device has luminance of 50 cd/m² and current efficiency of 0.02 cd/A.

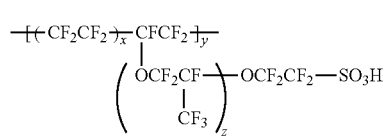

<Polymer 26>

(In the polymer 1, x=1300, y=200, and z=1)

Manufacturing Example 7—Manufacture of Light Emitting Device

An organic-inorganic-hybrid perovskite light emitting device was manufactured using the same method as Manufacturing Example 6, except that the method of Embodiment was used. The manufactured light emitting device has luminance of 40 cd/m² and current efficiency of 0.015 cd/A.

Manufacturing Example 8—Manufacture of Light Emitting Device

An organic-inorganic-hybrid perovskite light emitting device was manufactured using the same method as Manufacturing Example 6, except that the method of Manufacturing Example 4 was used. The manufactured light emitting device has luminance of 45 cd/m² and current efficiency of 0.018 cd/A.

Manufacturing Example 9—Manufacture of Light Emitting Device

An organic-inorganic-hybrid perovskite light emitting device was manufactured using the same method as Manufacturing Example 6, except that the method of Manufacturing Example 5 was used. The manufactured light emitting device has luminance of 60 cd/m² and current efficiency of 0.03 cd/A.

Manufacturing Example 10—Manufacture of Solution Including Inorganic Metal Halide Perovskite Nanoparticle The inorganic metal halide perovskite nanocrystal particle according to an embodiment of the present invention was formed. The inorganic metal halide perovskite nanocrystal particle was formed through an inverse nano-emulsion method, or reprecipitation method, or reprecipitation method, or hot injection method.

Particularly, $Cs_2CO_3$ and an oleic acid were added to octadecene (ODE) that is a non-polar solvent to react at a high temperature, thereby preparing a third solution. PbBr2, the oleic acid, and oleylamine were added to the non-polar solvent to react for one hour at a high temperature (120° C.), thereby preparing a fourth solution.

Then, the third solution slowly dropped drop wise into the fourth solution that is being strongly stirred to form the inorganic metal halide perovskite ($CsPbBr_3$) nanocrystal particle light-emitter having the 3D structure.

Thus, a solution including the inorganic metal halide perovskite nanoparticle was manufactured.

Manufacturing Example 11—Manufacture of Light Emitting Layer

The same process as Manufacturing Example 2 was performed except that the solution including the inorganic metal halide perovskite nanoparticles according to Manufacturing Example 10 instead of Manufacturing Example 1.

Manufacturing Example 12—Manufacture of Solar Cell

A solar cell according to an embodiment of the present invention was manufactured.

First, after an ITO substrate (a glass substrate coated with an ITO anode) is performed, PEDOT:PSS (CLEVIOS PH of Heraeus company) that is a conductive material was spin-coated on the ITO anode and then thermally treated for minutes at a temperature of 150° C. to form a hole extraction layer having a thickness of 40 nm.

The organic-inorganic-hybrid perovskite nanocrystal particle manufactured according to Manufacturing Example 1 was mixed with Phenyl-C61-butyric acid methyl ester (PCBM) and then applied to the hole extraction layer to form a photoactive layer, and Al having a thickness of 100 nm was deposited on the photoactive layer to manufacture a perovskite nanocrystal particle solar cell.

Comparative Example 1

An organic-inorganic-hybrid perovskite (OIP film) having a thin film shape was manufactured.

Particularly, $(CH_3NH_3)_2PbBr_4$ was dissolved in dimethylformamide that is a polar solvent to manufacture a first solution, and then, the first solution was spin-coated on a glass substrate to manufacture a $(CH_3NH_3)_2PbBr_4$ thin film.

Comparative Example 2

An organic-inorganic-hybrid perovskite (OIP film) having a thin film shape was manufactured.

Particularly, $(CH_3NH_3)_2PbCl_4$ was dissolved in dimethylformamide that is a polar solvent to manufacture a first solution, and then, the first solution was spin-coated on a glass substrate to manufacture a $(CH_3NH_3)_2PbCl_4$ thin film.

Experimental Example

Figure 14:
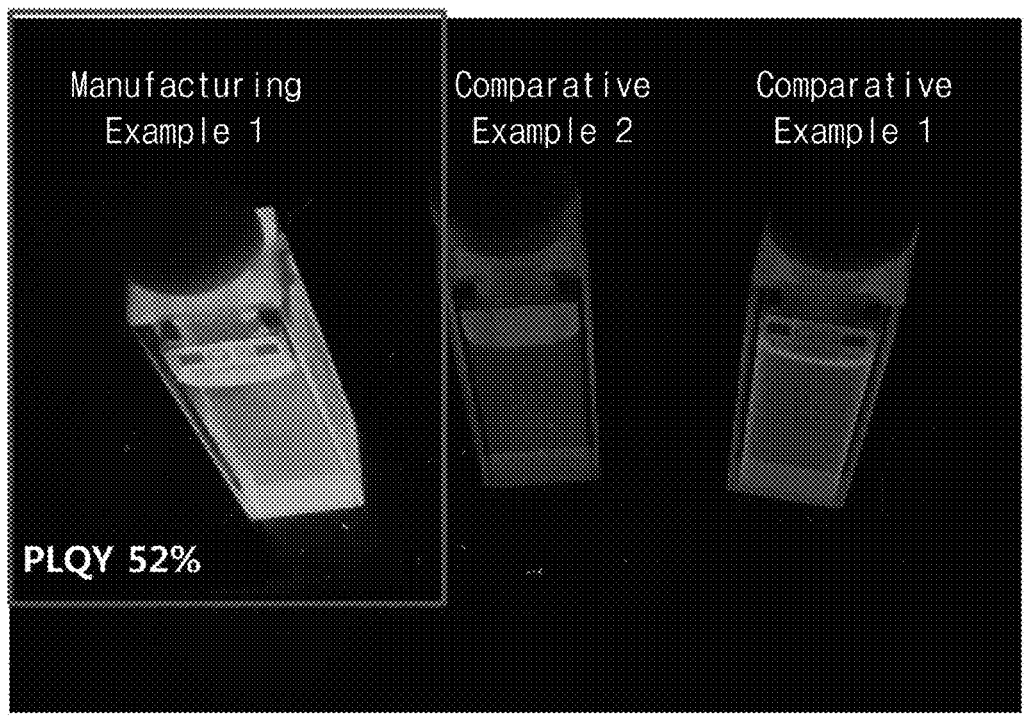
FIG. 14 is a fluorescent image obtained by photographing a organic-inorganic-hybrid perovskite nanoparticle including an organic-inorganic-hybrid perovskite nanocrystal structure according to Manufacturing Example 1 and an organic-inorganic-hybrid perovskite (OIP film) according to Comparative Example 1 and Comparative Example 2 by irradiating ultraviolet rays.

FIG. 14 is a fluorescent image obtained by photographing an organic-inorganic-hybrid perovskite nanoparticle including an organic-inorganic-hybrid perovskite nanocrystal structure according to Manufacturing Example 1 and an organic-inorganic-hybrid perovskite (OIP film) according to Comparative Example 1 and Comparative Example 2 by irradiating ultraviolet rays.

Referring to FIG. 14, it is seen that an organic-inorganic-hybrid perovskite, which is not in the form of a nanoparticle, but in the form of a thin film, according to Comparative Example 1 and Comparative Example 2 emits dark light, but the wavelength conversion particle having the nanoparticle shape according to Manufacturing Example emits very bright green light.

Also, as a result of measuring the photoluminescence quantum yield (PLQY), it is seen that the organic-inorganic-hybrid perovskite nanocrystal particle according to Manufacturing Example has a very high value.

On the other hand, in Comparative Example 1 and Comparative Example 2, the organic-inorganic-hybrid perovskite having the form of the thin film had a PLQY value of about 1%.

FIG. 15 is a schematic view of a nanoparticle according to Manufacturing Example and Comparative Example 1.

FIG. 15(a) is a schematic view of a light emitting material according to Comparative Example 1, FIG. 15(b) is a schematic view of an organic-inorganic-hybrid perovskite nanoparticle including the organic-inorganic-hybrid perovskite nanocrystal structure according to Manufacturing Example 1. Referring to FIG. 15(a), the organic-inorganic-hybrid perovskite nanoparticle according to Comparative Example 1 has the form of the thin film manufactured. Referring to FIG. 15(b), the wavelength conversion particle according to Manufacturing Example 1 has the form of the nanoparticle 110.

Figure 16:
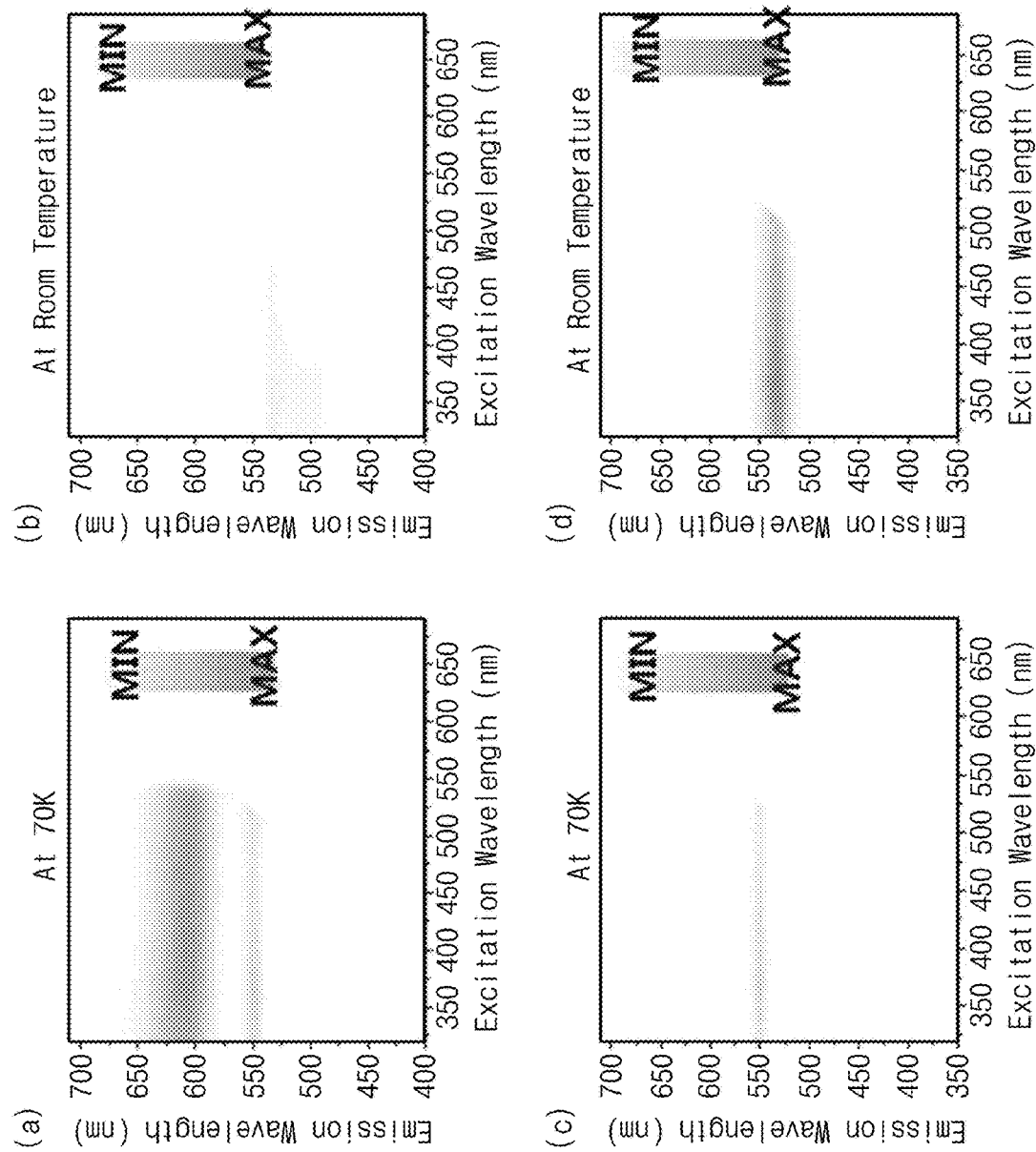
FIG. 16 is an image obtained by photographing a photoluminescence matrix of the nanoparticle at room temperature and a low temperature according to Manufacturing Example 1 and Comparative Example 1.

FIG. 16 is an image obtained by photographing a photoluminescence matrix of the nanoparticle at room temperature and a low temperature according to Manufacturing Example 1 and Comparative Example 1.

FIG. 16(a) is an image obtained by photographing a light emission matrix of the thin film-shaped organic-inorganic-hybrid perovskite (OIP film) according to Comparative Example 1 at a low temperature (70 K), and FIG. 16(b) is an image obtained by photographing a light emission matrix of the thin film-shaped organic-inorganic-hybrid perovskite (OIP film) according to Comparative Example 1 at room temperature.

FIG. 16(c) is an image obtained by photographing a photoluminescence matrix of the organic-inorganic-hybrid perovskite nanoparticle including the organic-inorganic-hybrid perovskite nanocrystal structure according to Manufacturing Example 1 at a low temperature (70K), and FIG. 15(d) is an image obtained by photographing a photoluminescence matrix of the organic-inorganic-hybrid perovskite nanoparticle including the organic-inorganic-hybrid perovskite nanocrystal structure according to Manufacturing Example 1 at room temperature.

Referring to FIGS. 16(a) and 16(d), in case of the organic-inorganic-hybrid perovskite nanocrystal particle including the organic-inorganic-hybrid perovskite nanocrystal structure according to Manufacturing Example 1, it is seen that photoluminescence occurs at the same position as that of the organic-inorganic-hybrid perovskite having the thin film shaped according to Comparative Example 1, and color purity is further improved. Also, in case of the OIP-NP film according to Manufacturing Example, it is seen that photoluminescence having high color purity occurs at room temperature at the same position as that at the low temperature, and an intensity of the light emission is not reduced. On the other hand, the organic-inorganic-hybrid perovskite according to Comparative Example 1 has different color purity and light emission position at room temperature and low temperature, and exciton does not emit light due to thermal ionization and delocalization of charge carriers at room temperature and thus is separated as free charges and annihilated to cause low light emission intensity.

Figure 17:
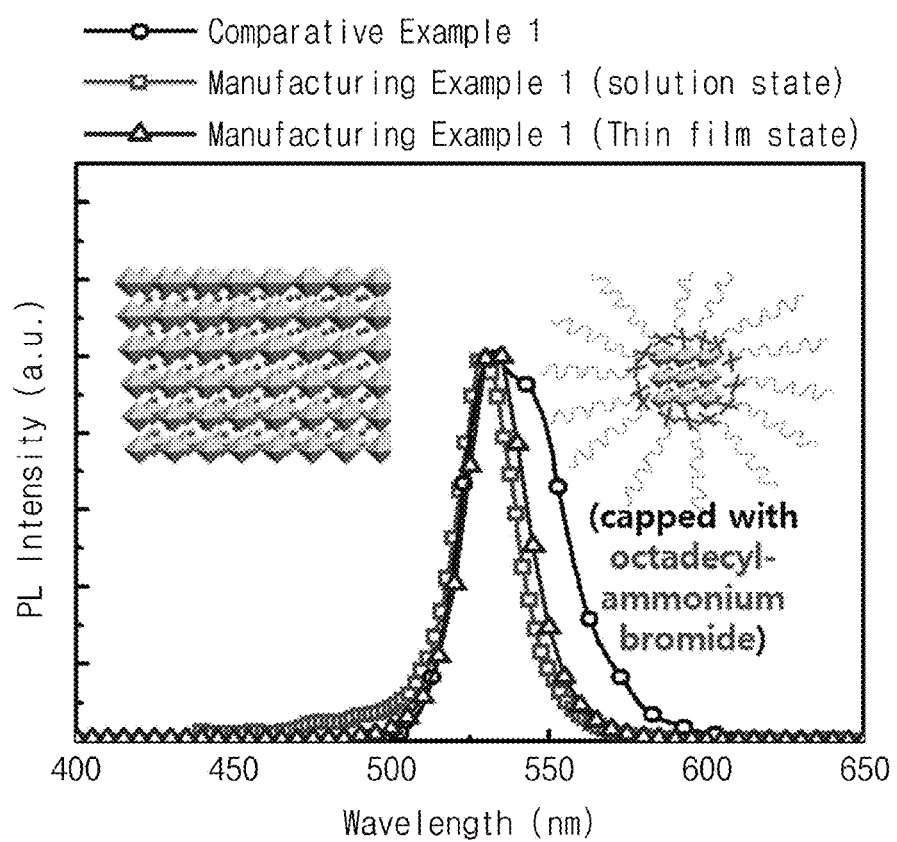
FIG. 17 is a graph obtained by photographing photoluminescence of the nanoparticle according to Manufacturing Example 1 and Comparative Example 1.

FIG. 17 is a graph obtained by photographing photoluminescence of the nanoparticle according to Manufacturing Example 1 and Comparative Example 1.

Referring to FIG. 17, in case of the liquid state in which the organic-inorganic-hybrid perovskite nanoparticle is contained in the solution according to Manufacturing Example 1, it is seen that the photoluminescence occurs at the same position as the existing organic-inorganic-hybrid perovskite according to Comparative Example 1, and color purity is further improved.

The organic-inorganic-hybrid perovskite nanocrystal having a crystal structure, in which the FCC and the BCC are combined with each other, may be formed in the first thin film of the nanoparticle, which includes the organic-inorganic-hybrid perovskite nanoparticle according to the present invention, the lamellar structure in which the organic plane and the inorganic plate are alternately stacked, may be formed, and the excitons may be confined in the inorganic plane to implement the high color purity.

Also, the exciton diffusion length may be reduced, and the exciton binding energy may increase in the nanocrystal particle having a size of 10 nm to 300 nm to prevent the excitons from being annihilated by the thermal ionization and the delocalization of the charge carriers, thereby improving the luminescent efficiency at room temperature.

Furthermore, since the organic-inorganic-hybrid perovskite is synthesized into the nanocrystal when compared to the 3D organic-inorganic-hybrid perovskite, the exciton binding energy may be improved to further improve the luminescent efficiency and the durability-stability.

Also, according to the method for manufacturing the first thin film of the nanoparticle, which includes the organic-inorganic-hybrid perovskite nanoparticle including the organic-inorganic-hybrid perovskite according to the present invention, the size of organic-inorganic-hybrid perovskite nanoparticle including the organic-inorganic-hybrid perovskite nanocrystal structure is adjusted in size according to the length and size of the alkyl halide surfactant.

While the present invention has been particularly shown and described with reference to the exemplary embodiments, it is to be understood that various changes and modifications may be made by those skilled in the art without departing from the spirit and scope of the present invention.

DESCRIPTION OF SYMBOLS

10: Substrate
20: First electrode
30: Exciton buffer layer
31: Conductive layer
32: Surface buffer
40: Light emitting layer
50: Second electrode

The invention claimed is:

1. A method of forming a light emitting layer, comprising steps of:
preparing a light emitting layer coating substrate; and
applying a solution comprising an organic-inorganic-hybrid perovskite nanoparticle comprising an organic-inorganic-hybrid perovskite nanocrystal structure on the light emitting layer coating substrate to form a first thin film of a nanoparticle,
wherein forming the first thin film comprises at least one process selected from perovskite-organic composite formation, spin-assembled nanocrystal layer formation using anchoring agents, solution process, dry-contact printing, a vacuum evaporation method, or floating process.

2. The method of claim 1, wherein the first thin film of the nanoparticle has a thickness of 1 nm to 1 µm.

3. The method of claim 1, wherein the first thin film of the nanoparticle has surface roughness of 0.1 nm to 50 nm.

4. The method of claim 1, wherein the step of applying the solution comprising the organic-inorganic-hybrid perovskite nanoparticle comprising the organic-inorganic-hybrid perovskite nanocrystal structure on the light emitting layer coating substrate to form the first thin film of the nanoparticle is repeatedly performed several times to adjust a thickness of the light emitting layer.

5. The method of claim 1, further comprising, before and after the step of forming the first thin film of the nanoparticle, a step of forming a second thin film of an organic-inorganic-hybrid perovskite microparticle or organic-inorganic-hybrid perovskite comprising the organic-inorganic-hybrid perovskite crystal structure on the light emitting layer coating substrate or the first thin film of the nanoparticle.

6. A photoactive layer comprising:
a coating substrate; and
a nanoparticle thin film disposed on the coating substrate, comprising the organic-inorganic-hybrid perovskite nanocrystal structure, and manufactured through the method of claim 1.

7. The method of claim 1, wherein the step of forming the first thin film of the nanoparticle uses a solution process.

8. The method of claim 7, wherein the solution process comprises at least one process selected from the group consisting of spin-coating, bar coating, slot-die coating, Gravure-printing, nozzle printing, ink-jet printing, screen printing, electrohydrodynamic jet printing, and electrospray.

9. The method of claim 1, wherein the step of forming the first thin film of the nanoparticle comprises steps of:
mixing an organic semiconductor with the solution comprising the organic-inorganic-hybrid perovskite nanoparticle to manufacture an organic-inorganic-hybrid perovskite-organic semiconductor solution; and
applying the organic-inorganic-hybrid perovskite-organic semiconductor solution to form the light emitting layer.

10. The method of claim 9, wherein, in the step of applying the organic-inorganic-hybrid perovskite-organic semiconductor solution to form the light emitting layer, the light emitting layer is self-organized in a shape in which an organic semiconductor layer and the organic-inorganic-hybrid perovskite nanoparticle are successively stacked on the light emitting layer coating substrate.

11. The method of claim 1, wherein the step of forming the first thin film of the nanoparticle comprises steps of:
forming a self-assembly monolayer on the light emitting layer coating substrate;
applying a solution comprising the organic-inorganic-hybrid perovskite nanoparticle on the self-assembly monolayer to form an organic-inorganic-hybrid perovskite nanoparticle layer; and
coming into contact with the organic-inorganic-hybrid perovskite nanoparticle layer by using a stamp to remove the organic-inorganic-hybrid perovskite nanoparticle layer by a desired pattern to form the organic-inorganic-hybrid perovskite nanoparticle layer on a second light emitting layer coating substrate.

12. The method of claim 11, wherein the stamp comprises at least one organic polymer selected from the group consisting of polyurethane), polydimethylsiloxane (PDMS), polyethylene oxide (PEO), polystyrene (PS), polycaprolactone (PCL), polyacrylonitrile (PAN), poly(methyl methacrylate) (PMMA), polyimide, poly(vinylidene fluoride) (PVDF), poly(n-vinylcarbazole) (PVK), and polyvinylchloride (PVC).

13. The method of claim 1, wherein the step of forming the first thin film of the nanoparticle comprises steps of:
preparing an anchoring solution and an organic-inorganic-hybrid perovskite nanoparticle solution comprising the organic-inorganic-hybrid perovskite nanocrystal structure;
applying the anchoring solution on the light emitting layer coating substrate to form an anchoring agent layer; and
applying the organic-inorganic-hybrid perovskite nanoparticle solution on the anchoring agent layer to form an anchored light emitting layer.

14. The method of claim 13, further comprising, after forming the anchoring light emitting layer, a step of forming a crosslinking agent layer on the anchored light emitting layer.

15. The method of claim 14, wherein the step of applying the organic-inorganic-hybrid perovskite nanoparticle solution and the step of forming the crosslinking agent layer on the layer coated with the organic-inorganic-hybrid perovskite nanoparticle solution are repeatedly performed to adjust a thickness of the light emitting layer.

16. A light emitting layer comprising:
a light emitting layer coating substrate; and
a light emitting layer disposed on the light emitting layer coating substrate and comprising the thin film of the nanoparticle, which comprises the organic-inorganic-hybrid perovskite nanocrystal structure and is manufactured through the method of claim 1.

17. The light emitting layer of claim 16, wherein the first thin film of the nanoparticle has a multilayer structure.

18. The light emitting layer of claim 16, wherein a second thin film of an organic-inorganic-hybrid perovskite microparticle or organic-inorganic-hybrid perovskite comprising the organic-inorganic-hybrid perovskite crystal structure is more disposed between the light emitting layer coating substrate and the first thin film of the nanoparticle or on the first thin film of the nanoparticle.

19. A light emitting device comprising:
a first electrode disposed on a substrate;
a light emitting layer disposed on the first electrode and comprising the first thin film of the nanoparticle, which comprises an organic-inorganic-hybrid perovskite nanocrystal structure and is manufactured through the method of claim 1.

20. The light emitting device of claim 19, wherein a second thin film of an organic-inorganic-hybrid perovskite microparticle or organic-inorganic-hybrid perovskite comprising the organic-inorganic-hybrid perovskite crystal structure is more disposed between the first electrode and the first thin film of the nanoparticle or on the first thin film of the nanoparticle.

21. The light emitting device of claim 19, further comprising an exciton buffer layer disposed between the first electrode and the light emitting layer and comprising a conductive material and a fluorine-based material having surface energy less than that of the conductive material.

22. The light emitting device of claim 19, wherein the first thin film of the nanoparticle has a multilayer structure.

23. A method of forming a light emitting layer, comprising steps of:
preparing a light emitting layer coating substrate; and
applying a solution comprising an inorganic metal halide perovskite nanoparticle comprising an inorganic metal halide perovskite nanocrystal structure on the light emitting layer coating substrate to form a first thin film of a nanoparticle,
wherein forming the first thin film comprises at least one process selected from perovskite-organic composite formation, spin-assembled nanocrystal layer formation using anchoring agents, solution process, dry-contact printing, a vacuum evaporation method, or floating process.

24. The method of claim 23, wherein the step of forming the first thin film of the nanoparticle uses a solution process.

25. The method of claim 24, wherein the solution process comprises at least one process selected from the group consisting of spin-coating, bar coating, slot-die coating, Gravure-printing, nozzle printing, ink-jet printing, screen printing, electrohydrodynamic jet printing, and electrospray.

26. A light emitting layer comprising:
a light emitting layer coating substrate; and
a light emitting layer disposed on the light emitting layer coating substrate and comprising the thin film of the nanoparticle, which comprises the inorganic metal halide perovskite nanocrystal structure and is manufactured through the method of claim 23.

\* \* \* \* \*